United States Patent
Cao et al.

(10) Patent No.: US 10,004,418 B2
(45) Date of Patent: Jun. 26, 2018

(54) ATRIAL ARRHYTHMIA EPISODE DETECTION IN A CARDIAC MEDICAL DEVICE

(71) Applicant: Medtronic, Inc., Minneapolis, MN (US)

(72) Inventors: Jian Cao, Shoreview, MN (US); Paul J DeGroot, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 61 days.

(21) Appl. No.: 14/604,411

(22) Filed: Jan. 23, 2015

(65) Prior Publication Data

US 2016/0213274 A1 Jul. 28, 2016

(51) Int. Cl.
| | |
|---|---|
| A61B 5/0456 | (2006.01) |
| A61N 1/37 | (2006.01) |
| A61B 5/0452 | (2006.01) |
| A61B 5/00 | (2006.01) |
| A61B 5/046 | (2006.01) |
| A61N 1/368 | (2006.01) |

(52) U.S. Cl.
CPC ............ *A61B 5/0456* (2013.01); *A61B 5/046* (2013.01); *A61B 5/04525* (2013.01); *A61B 5/4836* (2013.01); *A61B 5/686* (2013.01); *A61N 1/3702* (2013.01); *A61N 1/368* (2013.01)

(58) Field of Classification Search
CPC .......................... A61B 5/0456; A61B 5/04012
See application file for complete search history.

(56) References Cited

U.S. PATENT DOCUMENTS

| | | | |
|---|---|---|---|
| 4,226,245 | A | 10/1980 | Bennett |
| 4,374,382 | A | 2/1983 | Markowitz |
| 4,721,114 | A | 1/1988 | DuFault et al. |
| 5,117,824 | A | 6/1992 | Keimel et al. |
| 5,193,535 | A | 3/1993 | Bardy et al. |
| 5,292,338 | A | 3/1994 | Ihara |

(Continued)

FOREIGN PATENT DOCUMENTS

| | | |
|---|---|---|
| EP | 2572634 | 3/2013 |
| EP | 2572634 A1 | 3/2013 |

(Continued)

OTHER PUBLICATIONS

Sarkar et al, "Method and Apparatus for Atrial Arrhythmia Episode Detection", U.S. Appl. No. 14/695,135, filed Apr. 24, 2015, 30 pages.

(Continued)

*Primary Examiner* — Joseph Dietrich

(57) ABSTRACT

A method and medical device for identifying a cardiac waveform that includes sensing cardiac signals, determining a plurality of RR-intervals in response to the sensed cardiac signals, determining R-waves associated with the plurality of RR-intervals, determining P-waves in response to the determined R-waves, determining parameters associated with each P-wave, determining relative changes of the P-waves in response to the determined parameters, determining whether each of the P-waves match within a match threshold in response to the determined relative changes, and generating a P-wave template in response to each of the P-waves matching within the match threshold.

33 Claims, 12 Drawing Sheets

(56) References Cited

U.S. PATENT DOCUMENTS

| | | | |
|---|---|---|---|
| 5,312,445 A | 5/1994 | Nappholz et al. |
| 5,334,221 A | 8/1994 | Bardy |
| 5,458,623 A | 10/1995 | Lu et al. |
| 5,466,245 A | 11/1995 | Spinelli et al. |
| 5,545,186 A | 8/1996 | Olson et al. |
| 5,609,157 A | 3/1997 | Panescu |
| 5,609,158 A | 3/1997 | Chan |
| 5,755,739 A | 5/1998 | Sun |
| 5,782,888 A | 7/1998 | Sun |
| 5,817,134 A | 10/1998 | Greenhut |
| 6,067,473 A | 5/2000 | Greeninger et al. |
| 6,393,316 B1 | 5/2002 | Gillberg et al. |
| 6,470,210 B1 | 10/2002 | Chen et al. |
| 6,516,225 B1 | 2/2003 | Florio |
| 6,745,068 B2 | 6/2004 | Koyrakh et al. |
| 6,865,414 B1 | 3/2005 | Levine |
| 6,895,272 B2 | 5/2005 | Seim et al. |
| 6,904,315 B2 | 6/2005 | Panken et al. |
| 6,904,319 B2 | 6/2005 | Seim et al. |
| 6,912,418 B1 | 6/2005 | Florio |
| 6,922,584 B2 | 7/2005 | Wang et al. |
| 6,931,273 B2 | 8/2005 | Sippens |
| 7,031,765 B2 | 4/2006 | Ritscher et al. |
| 7,062,315 B2 | 6/2006 | Koyrakh et al. |
| 7,139,604 B1 | 11/2006 | Mouchawar |
| 7,184,815 B2 | 2/2007 | Kim et al. |
| 7,187,965 B2 | 3/2007 | Bischoff et al. |
| 7,242,978 B2 | 7/2007 | Cao et al. |
| 7,308,308 B1 | 12/2007 | Xi et al. |
| 7,412,282 B2 | 8/2008 | Houben |
| 7,509,160 B2 | 3/2009 | Bischoff et al. |
| 7,515,956 B2 | 4/2009 | Thompson |
| 7,532,928 B2 | 5/2009 | Lang |
| 7,537,569 B2 | 5/2009 | Sarkar et al. |
| 7,561,911 B2 | 7/2009 | Cao et al. |
| 7,570,990 B2 | 8/2009 | Faber |
| 7,580,748 B2 | 8/2009 | Garner |
| 7,593,766 B2 | 9/2009 | Faber |
| 7,596,405 B2 | 9/2009 | Kurzweil et al. |
| 7,623,911 B2 | 11/2009 | Sarkar et al. |
| 7,627,368 B2 | 12/2009 | Houben et al. |
| 7,640,054 B2 | 12/2009 | Koyrakh et al. |
| 7,657,305 B2 | 2/2010 | Nigam |
| 7,657,307 B2 | 2/2010 | Van Dam et al. |
| 7,706,869 B2 | 4/2010 | Cao et al. |
| 7,729,754 B2 | 6/2010 | Cao et al. |
| 7,826,893 B2 | 11/2010 | Cao et al. |
| 7,983,742 B2 | 7/2011 | Starc |
| 7,996,070 B2 | 8/2011 | van Dam et al. |
| 8,000,778 B2 | 8/2011 | Seim et al. |
| 8,064,998 B2 | 11/2011 | Good |
| 8,195,280 B2 | 6/2012 | Van Dam et al. |
| 8,233,980 B2 | 7/2012 | Pei |
| 8,265,753 B2 | 9/2012 | Higham |
| 8,280,510 B2 | 10/2012 | Dyjach et al. |
| 8,285,377 B2 | 10/2012 | Rosenberg |
| 8,412,316 B2 | 4/2013 | Seim et al. |
| 8,428,697 B2 | 4/2013 | Zhang et al. |
| 8,428,705 B2 | 4/2013 | Kurzweil et al. |
| 8,521,268 B2 | 8/2013 | Zhang et al. |
| 8,548,573 B2 | 10/2013 | Keefe |
| 8,560,058 B2 | 10/2013 | Babaeizadeh |
| 8,588,895 B2 | 11/2013 | Sanghera et al. |
| 8,639,316 B2 | 1/2014 | Sarkar |
| 8,688,469 B2 | 4/2014 | Ziegler et al. |
| 8,718,750 B2 | 5/2014 | Lian |
| 8,923,963 B2 | 12/2014 | Bonner et al. |
| 8,977,350 B2 | 3/2015 | Sarkar et al. |
| 9,433,791 B2 | 9/2016 | Warman et al. |
| 2002/0120206 A1 | 8/2002 | Taha et al. |
| 2003/0023178 A1 | 1/2003 | Bischoff et al. |
| 2005/0065564 A1 | 3/2005 | Seim et al. |
| 2005/0080347 A1 | 4/2005 | Sheth et al. |
| 2006/0074332 A1 | 4/2006 | Bischoff et al. |
| 2006/0079797 A1 | 4/2006 | Bischoff et al. |
| 2006/0079798 A1 | 4/2006 | Bischoff et al. |
| 2006/0106323 A1 | 5/2006 | Bischoff et al. |
| 2006/0167364 A1 | 7/2006 | Houben |
| 2007/0142866 A1 | 6/2007 | Li et al. |
| 2007/0203418 A1* | 8/2007 | Starc ............... A61B 5/04525 600/509 |
| 2007/0232944 A1 | 10/2007 | Ghanem et al. |
| 2008/0147133 A1 | 6/2008 | Garner |
| 2008/0154318 A1 | 6/2008 | Albus |
| 2008/0161703 A1 | 7/2008 | Houben et al. |
| 2009/0216144 A1 | 8/2009 | Hopenfeld |
| 2009/0270747 A1 | 10/2009 | van Dam et al. |
| 2010/0030293 A1 | 2/2010 | Sarkar et al. |
| 2010/0114195 A1 | 5/2010 | Burnes et al. |
| 2011/0125206 A1 | 5/2011 | Bornzin et al. |
| 2011/0208079 A1 | 8/2011 | Babaeizadeh et al. |
| 2011/0301661 A1 | 12/2011 | Seim et al. |
| 2011/0319949 A1 | 12/2011 | Bardy |
| 2012/0123232 A1 | 5/2012 | Najarian et al. |
| 2012/0226179 A1 | 9/2012 | Stadler et al. |
| 2012/0238891 A1 | 9/2012 | Sarkar et al. |
| 2012/0238892 A1 | 9/2012 | Sarkar |
| 2013/0172765 A1 | 7/2013 | Stewart |
| 2014/0128758 A1 | 5/2014 | Galloway et al. |
| 2014/0155722 A1 | 6/2014 | Greenspan et al. |
| 2014/0276154 A1 | 9/2014 | Katra et al. |
| 2014/0350422 A1 | 11/2014 | Stewart |
| 2014/0378851 A1 | 12/2014 | Frei et al. |
| 2015/0073295 A1 | 3/2015 | Gordon et al. |
| 2015/0080752 A1 | 3/2015 | Lian et al. |
| 2015/0105681 A1 | 4/2015 | Bonan et al. |
| 2015/0230722 A1 | 8/2015 | Sarkar et al. |
| 2015/0305642 A1 | 10/2015 | Reinke et al. |
| 2015/0306375 A1 | 10/2015 | Marshall et al. |
| 2015/0306410 A1 | 10/2015 | Marshall et al. |

FOREIGN PATENT DOCUMENTS

| | | |
|---|---|---|
| WO | 9809241 | 3/1998 |
| WO | 9809241 A1 | 3/1998 |
| WO | 01/80042 A1 | 10/2001 |
| WO | 2004108212 A2 | 12/2004 |
| WO | 2004043538 | 7/2008 |
| WO | 2012058398 A1 | 5/2012 |

OTHER PUBLICATIONS

Sarkar et al, "Method and Apparatus for Atrial Arrhythmia Episode Detection", U.S. Appl. No. 14/695,156, filed Apr. 24, 2015, 42 pages.

Sarkar et al, "Method and Apparatus for Atrial Arrhythmia Episode Detection", U.S. Appl. No. 14/695,171, filed Apr. 24, 2015, 38 pages.

Sarkar et al, "Method and Apparatus for Atrial Arrhythmia Episode Detection", U.S. Appl. No. 14/695,111, filed Apr. 24, 2015, 51 pages.

Cao et al, "Atrial Arrhythmia Episode Detection in a Cardiac Medical Device", U.S. Appl. No. 14/604,363, filed Jan. 23, 2015, 46 pages.

Cao et al, "Atrial Arrhythmia Episode Detection in a Cardiac Medical Device", U.S. Appl. No. 14/604,468, filed Jan. 23, 2015, 46 pages.

Zhang et al, "Method and Apparatus for Beat Acquisition During Template Generation in a Medical Device Having Dual Sensing Vectors", U.S. Appl. No. 14/604,111, filed Jan. 23, 2015, 77 pages.

Zhang et al, "Method and Apparatus for Beat Acquisition During Template Generation in a Medical Device Having Dual Sensing Vectors", U.S. Appl. No. 14/604,260, filed Jan. 23, 2015, 75 pages.

Zhang et al, "Method and Apparatus for Beat Acquisition During Template Generation in a Medical Device Having Dual Sensing Vectors", U.S. Appl. No. 15/002,521, filed Jan. 21, 2016, 80 pages.

Sarkar et al, "Method and Apparatus for Adjusting a Threshold During Atrial Arrhythmia Episode Detection in an Implantable Medical Device", U.S. Appl. No. 14/926,419, filed Oct. 29, 2015, 51 pages.

(56) References Cited

OTHER PUBLICATIONS

Sarkar et al, "Method and Apparatus for Identifying Sick Sinus Syndrome", U.S. Appl. No. 14/926,455, filed Oct. 29, 2015, 39 pages.
Cao et al, "Atrial Arrhythmia Episode Detection in a Cardiac Medical Device", U.S. Appl. No. 15/004,202, filed Jan. 22, 2016, 74 pages.
Cao et al, "Atrial Arrhythmia Detection During Intermittent Instances of Ventricular Pacing in a Cardiac Medical Device", U.S. Appl. No. 14/520,798, filed Oct. 22, 2014, 35 pages.
Cao et al, "Atrial Arrhythmia Detection During Ventricular Pacing in a Cardiac Medical Device", U.S. Appl. No. 14/520,847, filed Oct. 22, 2014, 49 pages.
Cao et al, "Atrial Arrhythmia Episode Detection in a Cardiac Medical Device", U.S. Appl. No. 14/520,938, filed Oct. 22, 2014, 47 pages.
"P-wave evidence as a method for improving algorithm to detect atrial fibrillation in insertable cardiac monitors", Helmut Purerfellner, MD. FHRS, et al., 2014 Heart Rhythm Society, vol. 11, No. 9, Sep. 2014, pp. 1575-1583.
Non Final Office Action, U.S. Appl. No. 14/604,363, dated Apr. 8, 2016, 6 pages.
Non Final Office Action, U.S. Appl. No. 14/604,468, dated Apr. 13, 2016, 7 pages.
Couceiro et al., "Detection of Atrial Fibrillation Using Model-Based ECG Analysis", 19th International Conference on Pattern Recognition, Dec. 2008, 5 pages.

* cited by examiner

ATRIAL ARRHYTHMIA EPISODE DETECTION IN A CARDIAC MEDICAL DEVICE

RELATED APPLICATION

Cross-reference is hereby made to commonly assigned U.S. patent application Ser. No. 14/604,363, filed on even date herewith entitled "ATRIAL ARRHYTHMIA EPISODE DETECTION IN A CARDIAC MEDICAL DEVICE", and U.S. patent application Ser. No. 14/604,468, filed on even date herewith entitled "ATRIAL ARRHYTHMIA EPISODE DETECTION IN A CARDIAC MEDICAL DEVICE", and incorporated by reference in its entirety.

TECHNICAL FIELD

The disclosure relates generally to cardiac medical devices and, in particular, to a method for detecting atrial arrhythmia episodes during ventricular pacing in a cardiac medical device.

BACKGROUND

During normal sinus rhythm (NSR), the heart beat is regulated by electrical signals produced by the sino-atrial (SA) node located in the right atrial wall. Each atrial depolarization signal produced by the SA node spreads across the atria, causing the depolarization and contraction of the atria, and arrives at the atrioventricular (A-V) node. The A-V node responds by propagating a ventricular depolarization signal through the bundle of His of the ventricular septum and thereafter to the bundle branches and the Purkinje muscle fibers of the right and left ventricles.

Atrial tachyarrhythmia includes the disorganized form of atrial fibrillation and varying degrees of organized atrial tachycardia, including atrial flutter. Atrial fibrillation (AF) occurs because of multiple focal triggers in the atrium or because of changes in the substrate of the atrium causing heterogeneities in conduction through different regions of the atria. The ectopic triggers can originate anywhere in the left or right atrium or pulmonary veins. The AV node will be bombarded by frequent and irregular atrial activations but will only conduct a depolarization signal when the AV node is not refractory. The ventricular cycle lengths will be irregular and will depend on the different states of refractoriness of the AV-node.

As more serious consequences of persistent atrial arrhythmias have come to be understood, such as an associated risk of relatively more serious ventricular arrhythmias and stroke, there is a growing interest in monitoring and treating atrial arrhythmias.

Methods for discriminating arrhythmias that are atrial in origin from arrhythmias originating in the ventricles have been developed for use in dual chamber implantable devices wherein both an atrial EGM signal and a ventricular EGM signal are available. Discrimination of arrhythmias can rely on event intervals (PP intervals and RR intervals), event patterns, and EGM morphology. Such methods have been shown to reliably discriminate ventricular arrhythmias from supra-ventricular arrhythmias. In addition, such methods have been developed for use in single chamber implantable devices, subcutaneous implantable devices, and external monitoring devices, where an adequate atrial EGM signal having acceptable signal-to-noise ratio is not always available for use in detecting and discriminating atrial arrhythmias. However, such single chamber devices have been designed to monitor AF during non-paced ventricular rhythm. An exemplary method and device for detecting arrhythmias during ventricular pacing was recently described in commonly assigned U.S. patent application Ser. No. 14/520,798 to Cao et. al., U.S. patent application Ser. No. 14/520,847 to Cao et al., and U.S. patent application Ser. No. 14/520,938 to Cao et al. What is needed, therefore, is a method for improving specificity of monitoring atrial arrhythmias during a ventricular paced rhythm.

DETAILED DESCRIPTION

In the following description, references are made to illustrative embodiments for carrying out the methods described herein. It is understood that other embodiments may be utilized without departing from the scope of the disclosure.

In various embodiments, ventricular signals are used for determining successive ventricular cycle lengths for use in detecting atrial arrhythmias. The atrial arrhythmia detection methods do not require an electrode positioned within the atrium as an atrial signal source to directly sense the atrial signal within the heart; i.e., the device may be a single chamber device having an electrode positioned only within the ventricle, or a subcutaneous device having no electrode positioned within the heart. The methods presented herein may be embodied in software, hardware or firmware in implantable or external medical devices. Such devices include implantable monitoring devices having cardiac EGM/ECG monitoring capabilities and associated EGM/ECG sense electrodes, which may be intracardiac, epicardial, or subcutaneous electrodes.

The methods described herein can also be incorporated in implantable medical devices having therapy delivery capabilities, such as single chamber or bi-ventricular pacing systems or ICDs that sense the R-waves in the ventricles and deliver an electrical stimulation therapy to the ventricles. The atrial arrhythmia detection methods presently disclosed may also be incorporated in external monitors having ECG electrodes coupled to the patient's skin to detect R-waves, e.g. Holter monitors, or within computerized systems that analyze pre-recorded ECG or EGM data. Embodiments may further be implemented in a patient monitoring system, such as a centralized computer system which processes data sent to it by implantable or wearable monitoring devices.

Figure 1:
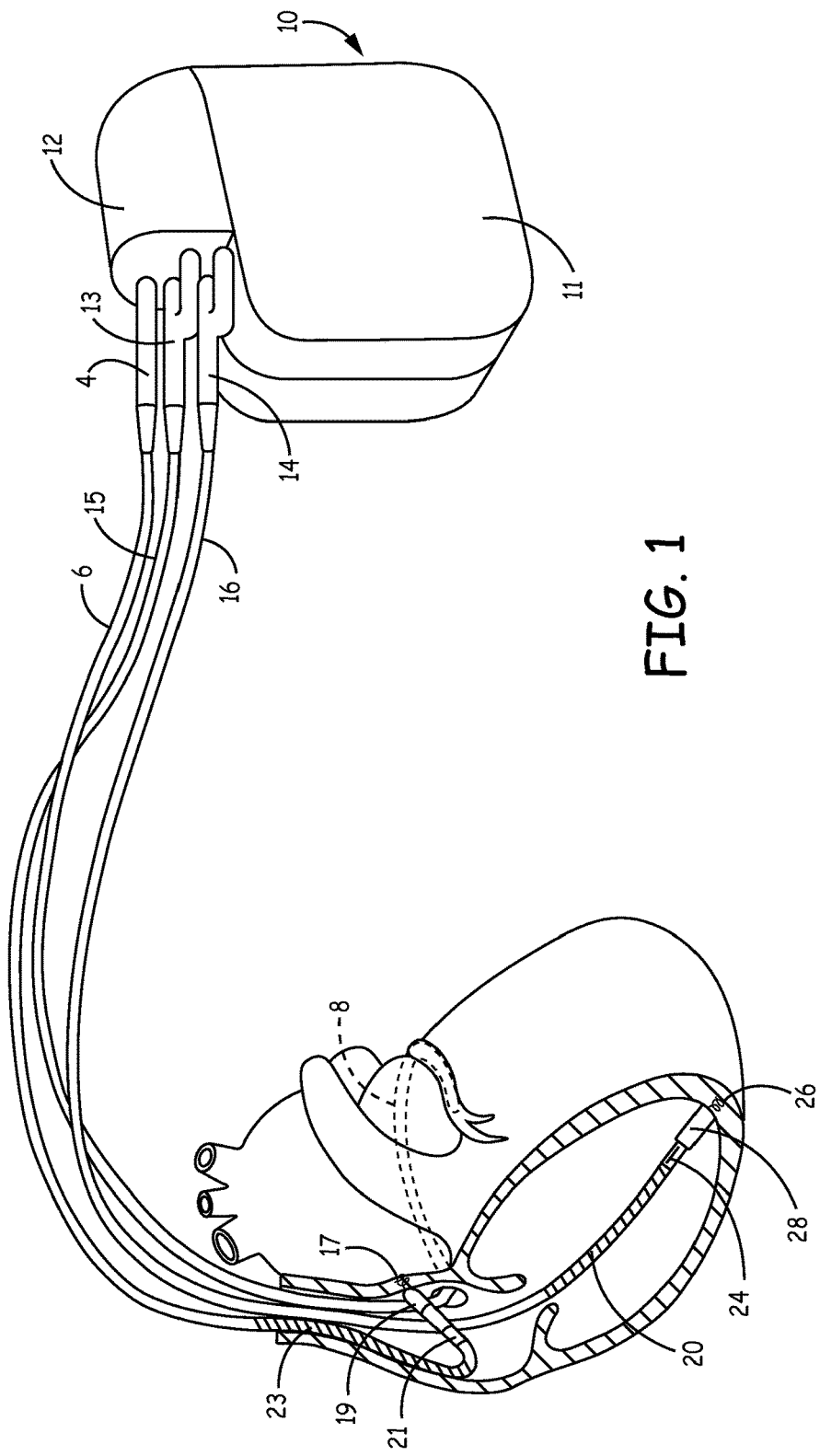
FIG. 1 is a schematic diagram of an exemplary medical device for detecting arrhythmia during ventricular pacing according to an embodiment of the present disclosure.

FIG. 1 is a schematic diagram of an exemplary medical device for detecting arrhythmia during ventricular pacing according to an embodiment of the present disclosure. As illustrated in FIG. 1, a medical device according to an embodiment of the present disclosure may be in the form of an implantable cardioverter defibrillator (ICD) 10 a connector block 12 that receives the proximal ends of a right ventricular lead 16, a right atrial lead 15 and a coronary sinus lead 6, used for positioning electrodes for sensing and stimulation in three or four heart chambers. Right ventricular lead 16 is positioned such that its distal end is in the right ventricle for sensing right ventricular cardiac signals and delivering pacing or shocking pulses in the right ventricle. For these purposes, right ventricular lead 16 is equipped with a ring electrode 24, an extendable helix electrode 26 mounted retractably within an electrode head 28, and a coil electrode 20, each of which are connected to an insulated conductor within the body of lead 16. The proximal end of the insulated conductors are coupled to corresponding connectors carried by bifurcated connector 14 at the proximal end of lead 16 for providing electrical connection to the ICD 10. It is understood that although the device illustrated in FIG. 1 is a dual chamber device, other devices such as single chamber devices may be utilized to perform the technique of the present disclosure described herein.

The right atrial lead 15 is positioned such that its distal end is in the vicinity of the right atrium and the superior vena cava. Lead 15 is equipped with a ring electrode 21 and an extendable helix electrode 17, mounted retractably within electrode head 19, for sensing and pacing in the right atrium. Lead 15 is further equipped with a coil electrode 23 for delivering high-energy shock therapy. The ring electrode 21, the helix electrode 17 and the coil electrode 23 are each connected to an insulated conductor with the body of the right atrial lead 15. Each insulated conductor is coupled at its proximal end to a connector carried by bifurcated connector 13.

The coronary sinus lead 6 is advanced within the vasculature of the left side of the heart via the coronary sinus and great cardiac vein. The coronary sinus lead 6 is shown in the embodiment of FIG. 1 as having a defibrillation coil electrode 8 that may be used in combination with either the coil electrode 20 or the coil electrode 23 for delivering electrical shocks for cardioversion and defibrillation therapies. In other embodiments, coronary sinus lead 6 may also be equipped with a distal tip electrode and ring electrode for pacing and sensing functions in the left chambers of the heart. The coil electrode 8 is coupled to an insulated conductor within the body of lead 6, which provides connection to the proximal connector 4.

The electrodes 17 and 21 or 24 and 26 may be used as true bipolar pairs, commonly referred to as a "tip-to-ring" configuration. Further, electrode 17 and coil electrode 20 or electrode 24 and coil electrode 23 may be used as integrated bipolar pairs, commonly referred to as a "tip-to-coil" configuration. In accordance with the invention, ICD 10 may, for example, adjust the electrode configuration from a tip-to-ring configuration, e.g., true bipolar sensing, to a tip-to-coil configuration, e.g., integrated bipolar sensing, upon detection of oversensing in order to reduce the likelihood of future oversensing. In other words, the electrode polarities can be reselected in response to detection of oversensing in an effort to reduce susceptibility of oversensing. In some cases, electrodes 17, 21, 24, and 26 may be used individually in a unipolar configuration with the device housing 11 serving as the indifferent electrode, commonly referred to as the "can" or "case" electrode.

The device housing 11 may also serve as a subcutaneous defibrillation electrode in combination with one or more of the defibrillation coil electrodes 8, 20 or 23 for defibrillation of the atria or ventricles. It is recognized that alternate lead systems may be substituted for the three lead system illustrated in FIG. 1. While a particular multi-chamber ICD and lead system is illustrated in FIG. 1, methodologies included in the present invention may adapted for use with any single chamber, dual chamber, or multi-chamber ICD or pacemaker system, subcutaneous implantable device, or other internal or external cardiac monitoring device.

Figure 2:
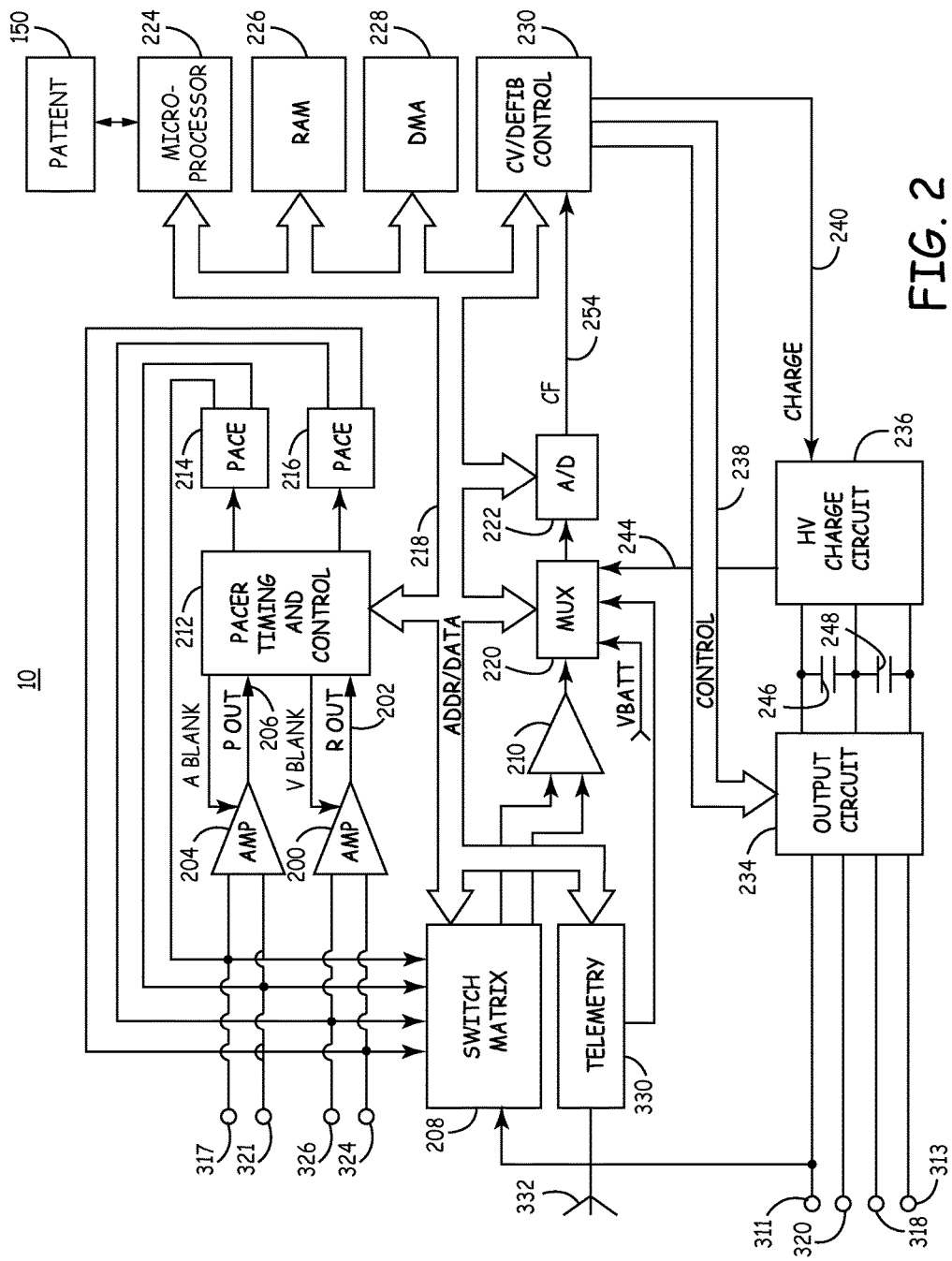
FIG. 2 is a functional schematic diagram of the medical device of FIG. 1.

FIG. 2 is a functional schematic diagram of the medical device of FIG. 1. This diagram should be taken as exemplary of the type of device with which the invention may be embodied and not as limiting. The disclosed embodiment shown in FIG. 2 is a microprocessor-controlled device, but the methods of the present invention may also be practiced with other types of devices such as those employing dedicated digital circuitry.

With regard to the electrode system illustrated in FIG. 1, ICD 10 is provided with a number of connection terminals for achieving electrical connection to the leads 6, 15, and 16 and their respective electrodes. A connection terminal 311 provides electrical connection to the housing 11 for use as the indifferent electrode during unipolar stimulation or sensing. The connection terminals 320, 313, and 318 provide electrical connection to coil electrodes 20, 8 and 23 respectively. Each of these connection terminals 311, 320, 313, and 318 are coupled to the high voltage output circuit 234 to facilitate the delivery of high energy shocking pulses to the heart using one or more of the coil electrodes 8, 20, and 23 and optionally the housing 11.

The connection terminals 317 and 321 provide electrical connection to the helix electrode 17 and the ring electrode 21 positioned in the right atrium. The connection terminals 317 and 321 are further coupled to an atrial sense amplifier 204 for sensing atrial signals such as P-waves. The connection terminals 326 and 324 provide electrical connection to the helix electrode 26 and the ring electrode 24 positioned in the right ventricle. The connection terminals 326 and 324 are further coupled to a ventricular sense amplifier 200 for sensing ventricular signals. The atrial sense amplifier 204 and the ventricular sense amplifier 200 preferably take the form of automatic gain controlled amplifiers with adjustable sensitivity. In accordance with the invention, ICD 10 and, more specifically, microprocessor 224 automatically adjusts the sensitivity of atrial sense amplifier 204, ventricular sense amplifier 200 or both in response to detection of oversensing in order to reduce the likelihood of oversensing. Ventricular sense amplifier 200 and atrial sense amplifier 204 operate in accordance with originally programmed sensing parameters for a plurality of cardiac cycles, and upon detecting oversensing, automatically provides the corrective action to avoid future oversensing. In this manner, the adjustments provided by ICD 10 to amplifiers 200 and 204 to avoid future oversensing are dynamic in nature. Particularly, microprocessor 224 increases a sensitivity value of the amplifiers, thus reducing the sensitivity, when oversensing is detected. Atrial sense amplifier 204 and ventricular sense amplifier 200 receive timing information from pacer timing and control circuitry 212.

Specifically, atrial sense amplifier 204 and ventricular sense amplifier 200 receive blanking period input, e.g., ABLANK and VBLANK, respectively, which indicates the amount of time the electrodes are "turned off" in order to prevent saturation due to an applied pacing pulse or defibrillation shock. As will be described, the blanking periods of atrial sense amplifier 204 and ventricular sense amplifier 200 and, in turn, the blanking periods of sensing electrodes associated with the respective amplifiers may be automatically adjusted by ICD 10 to reduce the likelihood of oversensing. The general operation of the ventricular sense amplifier 200 and the atrial sense amplifier 204 may correspond to that disclosed in U.S. Pat. No. 5,117,824, by Keimel, et al., incorporated herein by reference in its entirety. Whenever a signal received by atrial sense amplifier 204 exceeds an atrial sensitivity, a signal is generated on the P-out signal line 206. Whenever a signal received by the ventricular sense amplifier 200 exceeds a ventricular sensitivity, a signal is generated on the R-out signal line 202.

Switch matrix 208 is used to select which of the available electrodes are coupled to a wide band amplifier 210 for use in digital signal analysis. Selection of the electrodes is controlled by the microprocessor 224 via data/address bus 218. The selected electrode configuration may be varied as desired for the various sensing, pacing, cardioversion and defibrillation functions of the ICD 10. Specifically, microprocessor 224 may modify the electrode configurations based on detection of oversensing due to cardiac or non-cardiac origins. Upon detection of R-wave oversensing, for example, microprocessor 224 may modify the electrode configuration of the right ventricle from true bipolar sensing, e.g., tip-to-ring, to integrated bipolar sensing, e.g., tip-to-coil.

Signals from the electrodes selected for coupling to bandpass amplifier 210 are provided to multiplexer 220, and thereafter converted to multi-bit digital signals by A/D converter 222, for storage in random access memory 226 under control of direct memory access circuit 228 via data/address bus 218. Microprocessor 224 may employ digital signal analysis techniques to characterize the digitized signals stored in random access memory 226 to recognize and classify the patient's heart rhythm employing any of the numerous signal processing methodologies known in the art. An exemplary tachyarrhythmia recognition system is described in U.S. Pat. No. 5,545,186 issued to Olson et al, incorporated herein by reference in its entirety.

Upon detection of an arrhythmia, an episode of EGM data, along with sensed intervals and corresponding annotations of sensed events, are preferably stored in random access memory 226. The EGM signals stored may be sensed from programmed near-field and/or far-field sensing electrode pairs. Typically, a near-field sensing electrode pair includes a tip electrode and a ring electrode located in the atrium or the ventricle, such as electrodes 17 and 21 or electrodes 26 and 24. A far-field sensing electrode pair includes electrodes spaced further apart such as any of: the defibrillation coil electrodes 8, 20 or 23 with housing 11; a tip electrode 17 or 26 with housing 11; a tip electrode 17 or 26 with a defibrillation coil electrode 20 or 23; or atrial tip electrode 17 with ventricular ring electrode 24. The use of near-field and far-field EGM sensing of arrhythmia episodes is described in U.S. Pat. No. 5,193,535, issued to Bardy, incorporated herein by reference in its entirety. Annotation of sensed events, which may be displayed and stored with EGM data, is described in U.S. Pat. No. 4,374,382 issued to Markowitz, incorporated herein by reference in its entirety.

The telemetry circuit 330 receives downlink telemetry from and sends uplink telemetry to an external programmer, as is conventional in implantable anti-arrhythmia devices, by means of an antenna 332. Data to be uplinked to the programmer and control signals for the telemetry circuit are provided by microprocessor 224 via address/data bus 218. EGM data that has been stored upon arrhythmia detection or as triggered by other monitoring algorithms may be uplinked to an external programmer using telemetry circuit 330. Received telemetry is provided to microprocessor 224 via multiplexer 220. Numerous types of telemetry systems known in the art for use in implantable devices may be used.

The remainder of the circuitry illustrated in FIG. 2 is an exemplary embodiment of circuitry dedicated to providing cardiac pacing, cardioversion and defibrillation therapies. The pacer timing and control circuitry 212 includes programmable digital counters which control the basic time intervals associated with various single, dual or multi-chamber pacing modes or anti-tachycardia pacing therapies delivered in the atria or ventricles. Pacer circuitry 212 also determines the amplitude of the cardiac pacing pulses under the control of microprocessor 224.

During pacing, escape interval counters within pacer timing and control circuitry 212 are reset upon sensing of R-waves or P-waves as indicated by signals on lines 202 and 206, respectively. In accordance with the selected mode of pacing, pacing pulses are generated by atrial pacer output circuit 214 and ventricular pacer output circuit 216. The pacer output circuits 214 and 216 are coupled to the desired electrodes for pacing via switch matrix 208. The escape interval counters are reset upon generation of pacing pulses, and thereby control the basic timing of cardiac pacing functions, including anti-tachycardia pacing.

The durations of the escape intervals are determined by microprocessor 224 via data/address bus 218. The value of the count present in the escape interval counters when reset by sensed R-waves or P-waves can be used to measure R-R intervals and P-P intervals for detecting the occurrence of a variety of arrhythmias.

The microprocessor 224 includes associated read-only memory (ROM) in which stored programs controlling the operation of the microprocessor 224 reside. A portion of the random access memory (RAM) 226 may be configured as a number of recirculating buffers capable of holding a series of measured intervals for analysis by the microprocessor 224 for predicting or diagnosing an arrhythmia. In response to the detection of tachycardia, anti-tachycardia pacing therapy can be delivered by loading a regimen from microprocessor 224 into the pacer timing and control circuitry 212 according to the type of tachycardia detected. In the event that higher voltage cardioversion or defibrillation pulses are required, microprocessor 224 activates the cardioversion and defibrillation control circuitry 230 to initiate charging of the high voltage capacitors 246 and 248 via charging circuit 236 under the control of high voltage charging control line 240. The voltage on the high voltage capacitors is monitored via a voltage capacitor (VCAP) line 244, which is passed through the multiplexer 220. When the voltage reaches a predetermined value set by microprocessor 224, a logic signal is generated on the capacitor full (CF) line 254, terminating charging. The defibrillation or cardioversion pulse is delivered to the heart under the control of the pacer timing and control circuitry 212 by an output circuit 234 via a control bus 238. The output circuit 234 determines the electrodes used for delivering the cardioversion or defibrillation pulse and the pulse wave shape.

In one embodiment, the ICD 10 may be equipped with a patient notification system 150. Any patient notification method known in the art may be used such as generating perceivable twitch stimulation or an audible sound. A patient notification system may include an audio transducer that emits audible sounds including voiced statements or musical tones stored in analog memory and correlated to a programming or interrogation operating algorithm or to a warning trigger event as generally described in U.S. Pat. No. 6,067,473 issued to Greeninger et al., incorporated herein by reference in its entirety.

Figure 3:
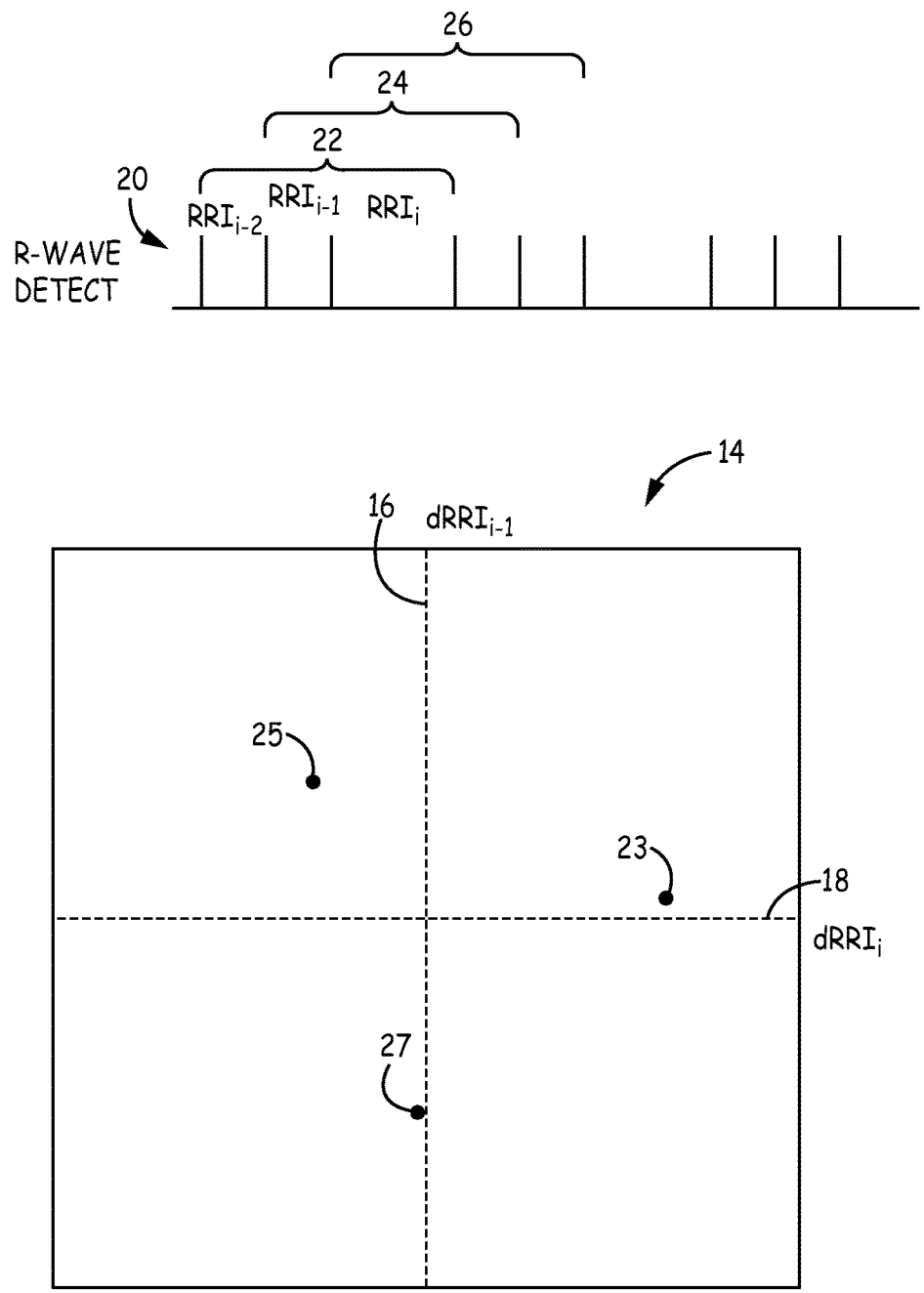
FIG. 3 is a schematic exemplary diagram of classifying of cardiac events in a cardiac medical device according to an embodiment of the present disclosure.

FIG. 3 is a schematic exemplary diagram of classifying of cardiac events in a cardiac medical device according to an embodiment of the present disclosure. Methods have been developed for detecting atrial arrhythmias based on the irregularity of ventricular cycles measured by RR intervals that exhibit discriminatory signatures when plotted in a Lorenz scatter plot such as the plot shown in FIG. 3. One such method is generally disclosed by Ritscher et al. in U.S. Pat. No. 7,031,765, incorporated herein by reference in its entirety. Other methods are generally disclosed by Sarkar, et al. in U.S. Pat. No. 7,623,911 and in U.S. Pat. No. 7,537,569 and by Houben in U.S. Pat. No. 7,627,368, all of which patents are also incorporated herein by reference in their entirety. Therefore, according to one embodiment, in order to determine whether an atrial fibrillation event is occurring, the device may plot RR intervals between determined sensed R-waves using a Lorentz scatter plot and make the decision as to whether an atrial fibrillation event is occurring based on the resulting interval differences determined from the plotted intervals. While the method of distinguishing atrial events according to the present disclosure is described using a scatter plot to determine RR intervals that exhibit discriminatory signatures, it is understood that the present disclosure may be utilized as part of any known methods for discriminating atrial fibrillation events.

In particular, as illustrated in FIG. 3, during the generation of a Lorenz scatter plot of VCL data for use in detecting atrial arrhythmias, the differences between consecutive RR intervals ($\delta RRs$) are plotted for a time series of R-R intervals (RRIs). The Lorenz plot 14 is a Cartesian coordinate system defined by $\delta RR_i$ along the x-axis 18 and $\delta RR_{i-1}$ along the y-axis 16. As such, each plotted point in a Lorenz plot is defined by an x-coordinate equaling $\delta RR_i$ and a y-coordinate equaling $\delta RR_{i-1}$. $\delta RR_i$ is the difference between the $i^{th}$ RRI and the previous RRI, $RRI_{i-1}$. $\delta RR_{i-1}$ is the difference between $RRI_{i-1}$ and the previous RRI, $RRI_{i-2}$. As such, each data point plotted on the Lorenz plot 14 represents a VCL pattern relating to three consecutive VCLs: $RRI_i$, $RRI_{i-1}$ and $RRI_{i-2}$, measured between four consecutively sensed R-waves. As noted previously, VCL information is not limited to detection of R-waves and determination of RRIs. The terms RRI and $\delta RR_i$ as used herein refer generally to a measurement of VCL and the difference between two consecutive VCL measurements, respectively, whether the VCL measurements were derived from a series of R-wave detections from an EGM or ECG signal or another ventricular cycle event detection from any other physiological signal (e.g. a peak pressure determined from a pressure signal). For the sake of illustration, the embodiments described herein often refer to R-wave detections for performing VCL measurements and the determination of ($\delta RR_i$, $\delta RR_{i-1}$) points.

As illustrated in FIG. 3, a series of R-wave events 20 are sensed and in order to plot a point on the Lorenz plot area 14, a ($\delta RR_i$, $\delta RR_{i-1}$) point may be determined by measuring successive RRIs determined from the R-wave events 20. In the example shown, a first series 22 of three consecutive RRIs ($RRI_{i-1}$, $RRI_{i-1}$ and $RRI_i$) provides the first data point on the Lorenz plot area 14. $\delta RR_{i-1}$, which is the difference between $RRI_{i-2}$ and $RRI_{i-1}$ is approximately 0. $\delta RR_i$, the difference between the $RRI_{i-1}$ and $RRI_i$, is a positive change. Accordingly, a ($\delta RR_i$, $\delta RR_{i-1}$) point 23 having a y-coordinate near 0 and a positive x-coordinate is plotted in the Lorenz plot 14, representing the first series 22.

The next series 24 of three RRIs provides the next ($\delta RR_i$, $\delta RR_{i-1}$) point 25 having a negative x-cooridinate ($RRI_i$ being less than $RRI_{i-1}$) and a positive y-coordinate ($RRI_{i-1}$ being greater than $RRI_{i-2}$). This process of plotting ($\delta RR_i$, $\delta RR_{i-1}$) points continues with the three cycle series 26 providing data point 27 and so on.

Figure 4:
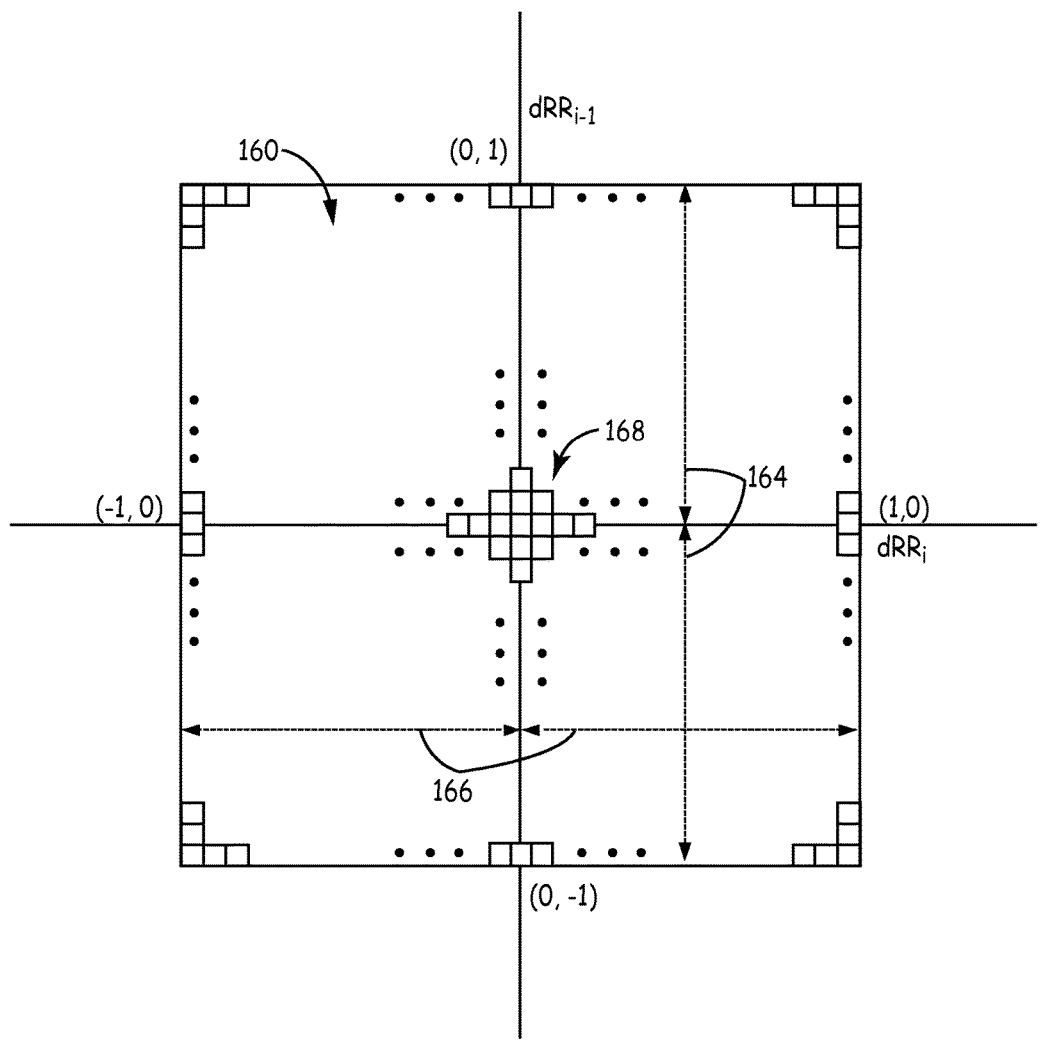
FIG. 4 is a diagram of an exemplary two-dimensional histogram representing a Lorenz plot area for identifying cardiac events.

FIG. 4 is a diagram of an exemplary two-dimensional histogram representing a Lorenz plot area for identifying cardiac events. Generally, the Lorenz plot area 14 shown in FIG. 4 is numerically represented by a two-dimensional histogram 160 having predefined ranges 166 and 164 in both positive and negative directions for the $\delta RR_i$ and $\delta RR_{i-1}$ coordinates, respectively. The two-dimensional histogram is divided into bins 168 each having a predefined range of $\delta RR_i$ and $\delta RR_{i-1}$ values. In one example, the histogram range might extend from −1200 ms to +1200 ms for both $\delta RR_i$ and $\delta RR_{i-1}$ values, and the histogram range is divided into bins extending 7.5 ms in each of the two dimensions resulting in a 160 bin×160 bin histogram. The successive RRI differences determined over a detection time interval are used to populate the histogram 160. Each bin stores a count of the number of ($\delta RR_i$, $\delta RR_{i-1}$) data points falling into the bin range. The bin counts may then be used in determining RRI variability metrics and patterns for determining a cardiac rhythm type.

An RRI variability metric is determined from the scatter plot. Generally, the more histogram bins that are occupied, i.e. the more sparse the distribution of ($\delta RR_i$, $\delta RR_{i-1}$) points, the more irregular the VCL during the data acquisition time period. As such, a metric of the RRI variability can be used for detecting atrial fibrillation, which is associated with highly irregular VCL. In one embodiment, an RRI variability metric for detecting AF, referred to as an AF score is computed as generally described in the above-incorporated '911 patent. Briefly, the AF score may be defined by the equation:

$$\text{AF Evidence}=\text{Irregularity Evidence}-\text{Origin Count}-\text{PAC Evidence}$$

wherein Irregularity Evidence is the number of occupied histogram bins outside a Zero Segment defined around the origin of the Lorenz plot area. During normal sinus rhythm or highly organized atrial tachycardia, nearly all points will fall into the Zero Segment because of relatively small, consistent differences between consecutive RRIs. A high number of occupied histogram bins outside the Zero segment is therefore positive evidence for AF.

The Origin Count is the number of points in a "Zero Segment" defined around the Lorenz plot origin. A high Origin Count indicates regular RRIs, a negative indicator of atrial fibrillation, and is therefore subtracted from the Irregularity Evidence term. In addition, a regular PAC evidence score may be computed as generally described in the above-incorporated '911 patent. The regular PAC evidence score is computed based on a cluster signature pattern of data points that is particularly associated with PACs that occur at regular coupling intervals and present regular patterns of RRIs, e.g. associated with bigeminy (short-short-long RRIs) or trigeminy (short-short-short-long RRIs).

In other embodiments, an AF score or other RRI variability score for classifying an atrial rhythm may be computed as described in any of the above-incorporated '765, '316, '911, '569 and '368 patents.

The AF score is compared to an AF threshold for detecting atrial fibrillation to determine whether the AF score corresponds to an AF event. The AF threshold may be selected and optimized based on historical clinical data of selected patient populations or historical individual patient data, and the optimal threshold setting may vary from patient to patient. If the metric crosses a detection threshold, AF detection occurs. A response to AF detection is made, either in response to a classification of a single two second time interval as being AF, i.e., being greater than the AF threshold, or in response to a predetermined number of two second intervals being classified as being an AF event by each being greater than the AF threshold. Such response to the AF detection may include withholding or altering therapy, such as a ventricular therapy, for example, storing data that can be later retrieved by a clinician, triggering an alarm to the patient or that may be sent remotely to alert the clinician, delivering or adjusting a therapy, and triggering other signal acquisition or analysis.

The RRI measurements may continue to be performed after an AF detection to fill the histogram during the next detection time interval. After each detection time interval, the RRI variability metric is determined and the histogram bins are re-initialized to zero for the next detection time interval. The new RRI variability metric determined at the end of each data acquisition interval may be used to determine if the AF episode is sustained or terminated.

Figure 5:
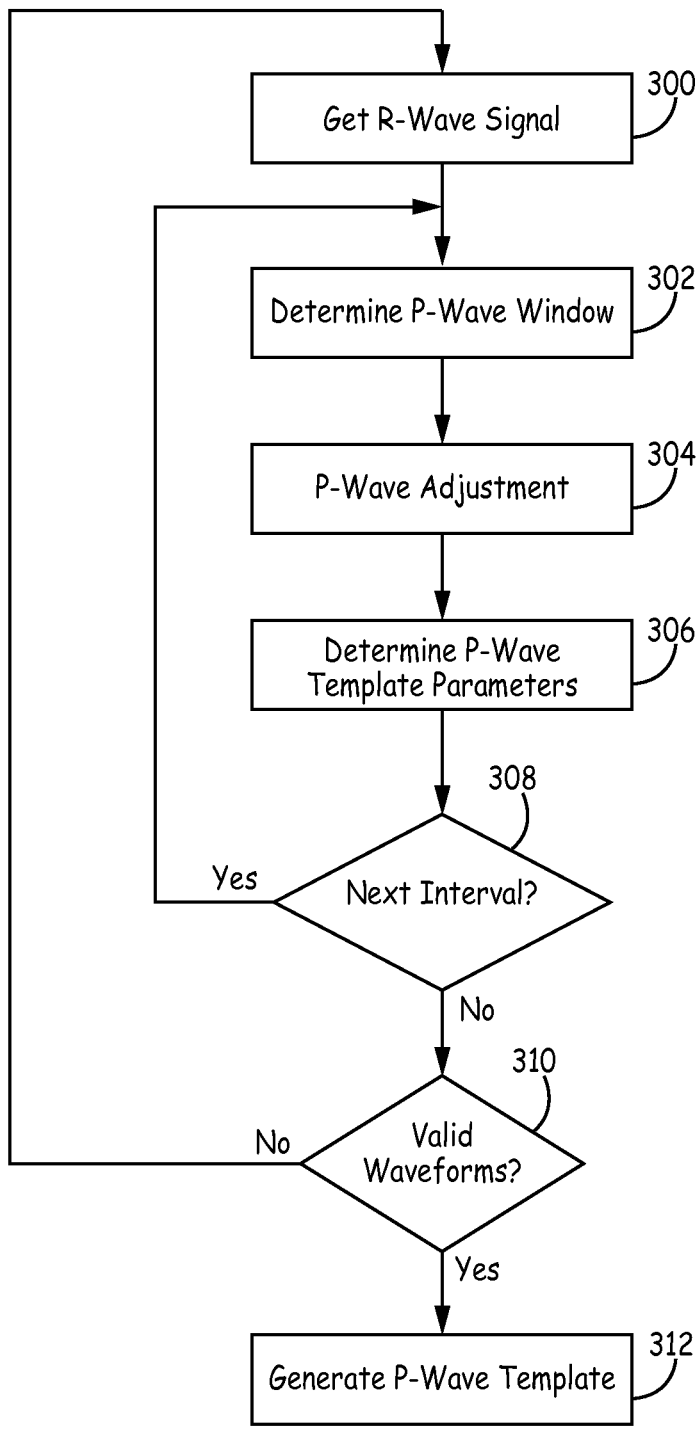
FIG. 5 is a flowchart of a method of generating a template for determining atrial fibrillation events in a medical device according to an embodiment of the present disclosure.

FIG. 5 is a flowchart of a method of generating a template for determining atrial fibrillation events in a medical device according to an embodiment of the present disclosure. Flow charts presented herein are intended to illustrate the functional operation of the device, and should not be construed as reflective of a specific form of software or hardware necessary to practice the invention. It is believed that the particular form of software will be determined primarily by the particular system architecture employed in the device and by the particular detection and therapy delivery methodologies employed by the device. Providing software to accomplish the present invention in the context of any modern IMD, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

As illustrated in FIG. 5, according to one embodiment, in order to generate a P-wave template, the device identifies a predetermined number of normal R-waves, i.e., R-waves associated with non-paced, slow rhythms, having a desired R-wave morphology, Block 300. The predetermined number of normal cardiac intervals, which may be either consecutive intervals or nonconsecutive intervals, are then used to generate the P-wave template, as described below in detail. For example, the device identifies an RR-interval from a QRS signal resulting from the sensed cardiac signal, and identifies the interval as being a normal cardiac interval if both the RR-interval is greater than a predetermine normal interval threshold, such 600 milliseconds, for example, and a morphology match of the RR-interval matches a predetermined morphology matching threshold. The morphology match may be determined using a known waveform matching scheme, such as a wavelet transform analysis scheme, or other known morphology matching scheme. Examples of ECG template acquisition and ECG signal analysis methods are generally disclosed in U.S. Pat. No. 6,393,316 to Gillberg, et al., U.S. Pat. No. 7,062,315 to Koyrakh, et al., and U.S. Pat. No. 7,996,070 to van Dam et al., incorporated herein by reference in their entireties.

According to one embodiment, for example, the device may determine whether four R-waves associated with four identified normal cardiac RR-intervals each have an individual predetermined morphology match score that identifies the R-wave as having a desired R-wave morphology. If one or more of the R-waves do not have the predetermined morphology match score identifying the R-wave as having the desired R-wave morphology, the process of identifying the predetermined number of R-waves is repeated to generate a new predetermined number of normal R-waves, and morphology matches are again determined for the newly generated normal R-waves, Block 300.

Once the predetermined number of normal R-waves having corresponding R-waves with the desired R-wave morphology are identified in Block 300, the device determines a P-wave window for each of the predetermined number of R-waves, Block 302. The P-wave window is used to identify a P-wave associated with each R-wave. Upon identification of the P-wave using the P-wave window, the device performs a P-wave adjustment for each identified P-wave, Block 304, and determines P-wave template parameters associated with each P-wave, Block 306, as will be described in detail below. Once the P-waves associated with each of the R-waves have been identified, Block 302, the P-wave adjustment has been made, Block 304, and the P-wave template parameters have been determined, Block 306, for each of the predetermined number of P-waves, No in Block 308, the device determines whether the P-waves are valid template generation waveforms, Block 310, using the determined P-wave template parameters, Block 306, as will be described in detail below. If any of the predetermined P-waves are determined not to be a valid template generation waveform, No in Block 310, the process of identifying the predetermined number of normal RR-intervals is repeated to generate new resulting R-waves, morphology matches are again determined for the newly generated R-waves, Block 300, and the waveform validation process Blocks 302-310, is repeated. If all of the predetermined P-waves are determined to be valid template generation waveforms, Yes in Block 310, the P-wave template is generated using the valid waveforms, Block 312, as will be described in detail below.

Figure 6A:
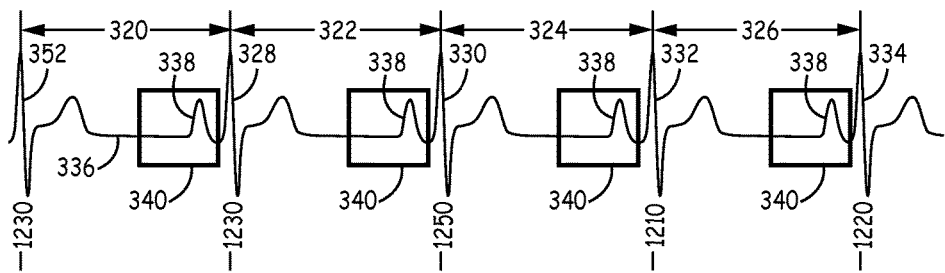
FIGS. 6A and 6B are schematic diagrams of identifying a P-wave portion of a sensed cardiac signal in a medical device according to an embodiment of the present disclosure.
Figure 6B:
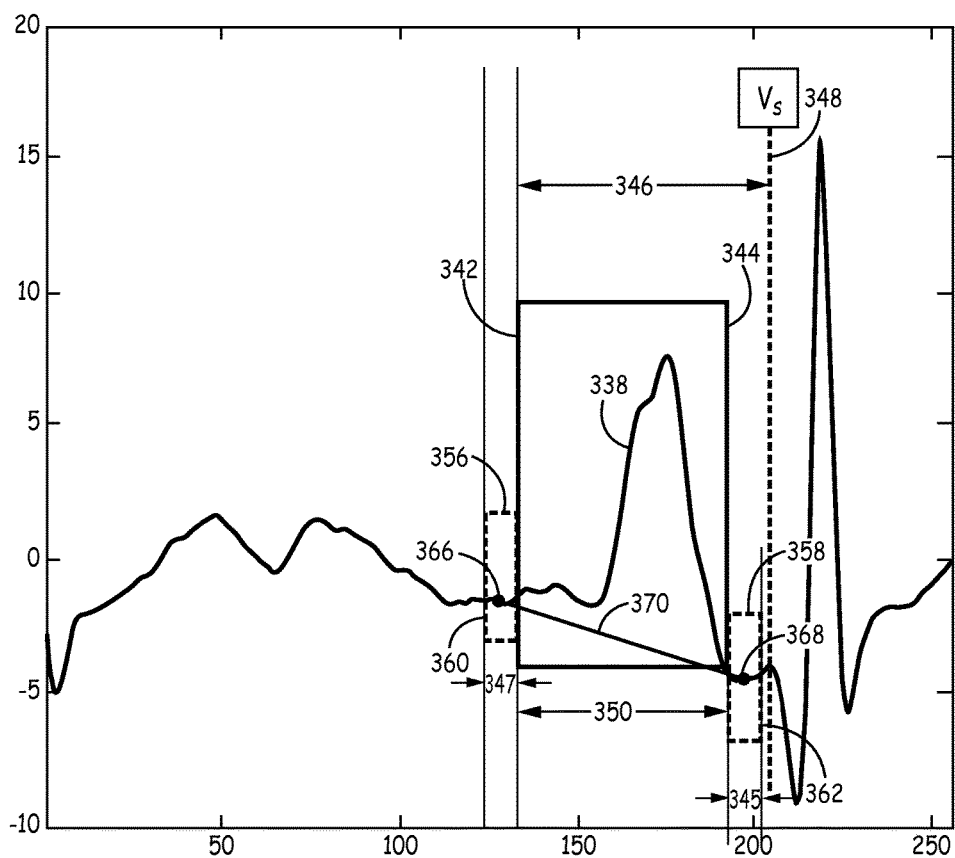

FIGS. 6A and 6B are schematic diagrams of identifying a P-wave portion of a sensed cardiac signal in a medical device according to an embodiment of the present disclosure. As illustrated in FIG. 6A, the device identifies four normal RR-intervals 320-326 associated with four sensed R-waves 328-334 of a sensed cardiac signal 336, and determines that the corresponding R-waves 328-334 each have the desired R-wave morphology, as described above. In order to identify a P-wave portion 338 for each of the predetermined number of R-waves 328-334, the device determines a P-wave window 340 for each R-wave 328-334. For example, as illustrated in FIG. 6B, in order to determine the P-wave window 340 associated with each R-wave 328-334, the device determines a P-wave window start point 342 and a P-wave window end point 344 based on sensing of the R-wave 328-334. For example, the P-wave window start point 342 is determined to be located a predetermined distance 346 prior to a Vs event 348 associated with the identified R-wave 328 of the cardiac signal 336, and the corresponding P-wave window end point 344 is determined to extend a predetermined distance 350 from the P-wave window start point 342, such as 242 ms, for example.

Figure 7:
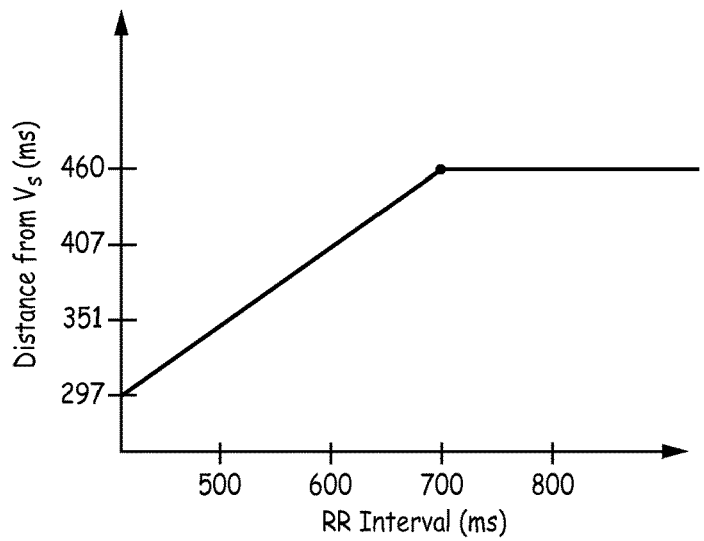
FIG. 7 is a graphical representation of determining of a P-wave window start point based on a sensed R-wave for generating a template during determining of atrial fibrillation events in a medical device according to an embodiment of the present disclosure.

FIG. 7 is a graphical representation of determining of a P-wave window start point based on a sensed R-wave for generating a template during determining of atrial fibrillation events in a medical device according to an embodiment of the present disclosure. According to one embodiment, the location of the window start point 342 relative to the Vs event 348 may be dependent upon the heart rate associate with the Vs sense event 348 for determining the RR-interval 320. For example, for R-wave 328, the device determines whether a length of the RR interval 320 between R-wave 328 and a previous R-wave 352 is greater than a predetermined RR interval threshold, such as 700 ms, for example, and sets the location of the window start point 342 based on the result.

In particular, according to one embodiment, if RR-interval 320 is greater than the RR-interval threshold, the predetermined distance 346 is set as a baseline distance of 460 ms, for example. However, if RR interval 320 is not greater than the RR-interval threshold, the predetermined distance 346 may be reduced from the baseline distance by an amount relative to the length of the determined RR interval 320. For example, according to one embodiment, the reduction in the distance 346 may as determined from the graph illustrated in FIG. 7, so that if the RR interval 320 is 600 ms, for example, the distance 346 is reduced from 460 ms to 406 ms; if the RR interval 320 is 500 ms, the distance 346 is reduced to 350 ms; and if the RR interval 320 is 400 ms, the distance 346 is reduced to 296 ms, and so forth. According to one embodiment, a distance 345 that the end point 344 is located relative to the Vs sense event 348 remains the same regardless of the location of the start point 342. For example, the distance 345 may be set as being the distance utilized when the length of the RR interval 320 between R-wave 328 and a previous R-wave 352 is greater than the predetermined RR interval threshold, during which the distance 345 is set as being approximately equal to 218 ms (460 ms–242 ms). In this way, as the magnitude of the RR intervals decreases, the width 346 of the P-wave window 342 is reduced since the distance 346 is reduced.

Figure 8A:
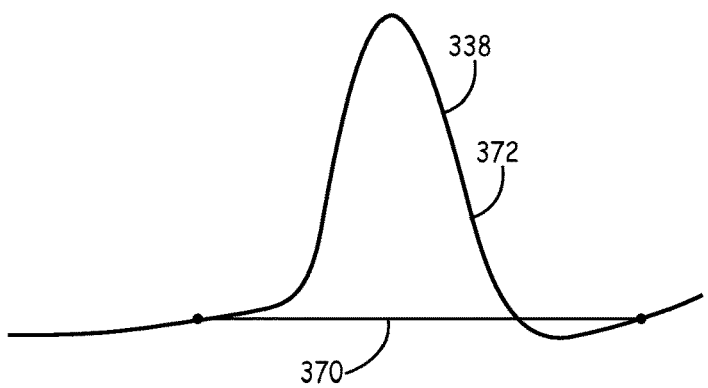
FIGS. 8A and 8B are schematic diagrams of determining of P-wave template parameters in a medical device according to an embodiment of the present disclosure.
Figure 8B:
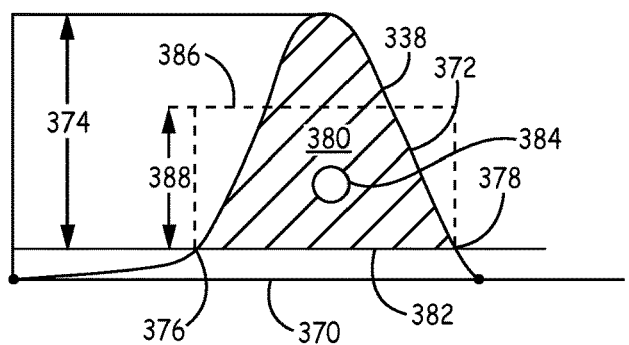

FIGS. 8A and 8B are schematic diagrams of determining of P-wave template parameters in a medical device according to an embodiment of the present disclosure. As can been seen in FIGS. 6A, 8A and 8B, in some instances the P-wave 328 may be shaped such that a beginning portion of the P-wave along the cardiac signal 336 is located at an amplitude that differs from an amplitude of an ending portion of the P-wave 328, resulting in a phenomena known as baseline wander. In order to account for this baseline wander, the device may determine a first baseline wander window 356 associated with the beginning portion of the P-wave and a second baseline wander window 358 associated with the ending portion of the P-wave. For example, according to one embodiment, illustrated in FIG. 6B, the device may determine that windows 356 and 358 are located outside of the P-wave window 340, with the first baseline wander window 356 extending between the P-wave window start point 342 and a baseline window start point 360 located a predetermined distance 347 prior to the P-wave window start point 342, such as 30 ms, for example, and the second baseline wander window 358 extending between the P-wave window end point 344 and a baseline window endpoint 362 located a predetermined distance from the P-wave window end point 344, such as 30 ms, for example. The device then determines both a first baseline end point 366 located within the first baseline wander window 356, and a second baseline end point 368 located within the second baseline wander window 358 based on the cardiac signal 336 within the respective windows 356 and 358. For example, endpoint 366 may be determined to be the average amplitude of the cardiac signal 336 within window 356, and endpoint 368 may be determined as being the average amplitude of the cardiac signal 336 within window 358. A P-wave baseline 370 therefore is determined to extend between endpoint 366 and endpoint 368, so that a linear adjustment of the P-wave is made by adjusting a slope of the baseline 370, resulting in a baseline adjusted P-wave 372 having approximately zero slope.

The device determines whether an absolute value of a maximum amplitude of the baseline adjusted P-wave 372 is greater than or equal to an absolute value of a minimum amplitude. If the absolute value of the maximum amplitude is greater than or equal to the absolute minimum amplitude, a maximum amplitude 374 of the baseline adjusted P-wave 372 is set equal to the absolute maximum amplitude, and the negative portion of the wave form 372 is set equal to zero. On the other hand, if the absolute value of the maximum amplitude is not greater than or equal to the absolute minimum amplitude, a maximum amplitude 374 of the baseline adjusted P-wave 372 is set equal to the absolute minimum amplitude, and the positive portion of the wave form 372 is set equal to zero.

The device determines a first minimum amplitude point 376 located along a first side of the adjusted P-wave 372 and a second minimum amplitude point 378 located along a second side of the adjusted P-wave 372 opposite the first side. According to an embodiment, the first minimum amplitude point 376 and the second minimum amplitude point 378 may be determined based on the maximum amplitude. For example, the device determines the first and second minimum points 376 and 378 as being located along the waveform 372 at a portion of the maximum amplitude 374, such as one sixteenth of the maximum amplitude 374, for example. The device then determines the area of a portion 380 (shown in hashed marks) of the adjusted P-wave 372 defined by a baseline 382 extending between points 376 and 378 of the adjusted P-wave 372.

In order to subsequently align the current four P-waves 338, the device determines a center of area 384 of each of the P-waves 338. According to one embodiment, for example, in order to approximate the center of area 384 of a P-wave, the device normalizes the area of the portion 380 of the adjusted P-wave 372 by determining a P-wave center window 386 that is a normalized rectangular version of the adjusted P-wave 372, having one side corresponding to the baseline 382 and an area approximating the area of the portion 380 of the P-wave 372 formed by baseline 382 and the determined maximum amplitude 374. Using the determined baseline 382 and area of the portion 380 of the P-wave 372, the device determines a normalized amplitude 388 of P-wave center window 386, and an approximate center of area 384 of the adjusted P-wave 372 is calculated based on the amplitude 388 and width 382 of the normalized center window 386. This determination of the linear adjustment of the P-wave and the approximate center of area 384 using a normalized center window 386 is performed for each P-wave 328 of the determined R-waves 328-334, and subsequently utilized to generate a P-wave template, and confirm a detected AF event, as described below.

Figure 9:
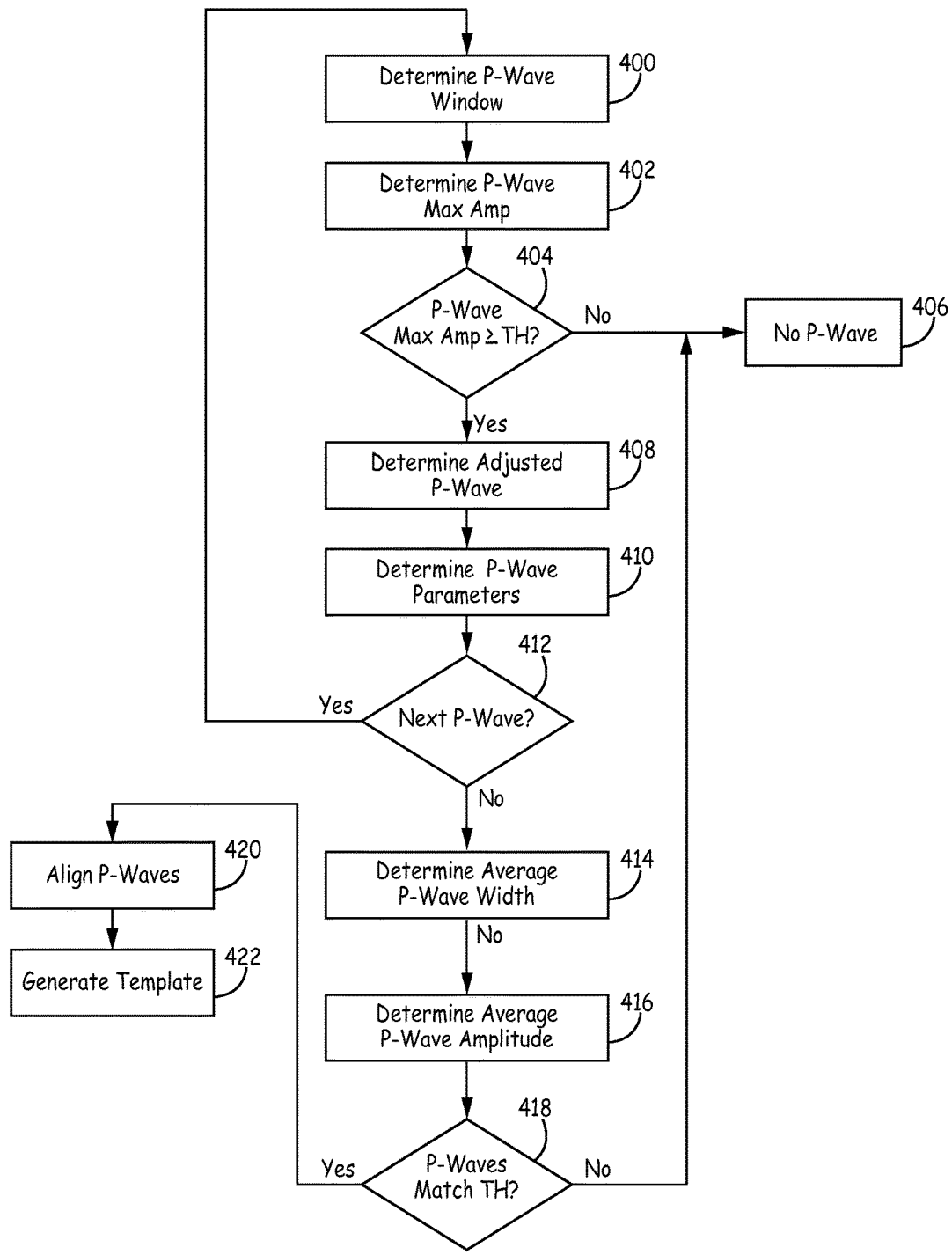
FIG. 9 is a flowchart of a method for generating a template for determining an atrial fibrillation event in a medical device according to an embodiment of the present disclosure.

FIG. 9 is a flowchart of a method for generating a template for determining an atrial fibrillation event in a medical device according to an embodiment of the present disclosure. As illustrated in FIG. 9, according to one embodiment, during generating of a P-wave template, the device senses four R-waves 328-334 and identifies four corresponding P-waves 338, as described above. For each P-wave 338, the device determines the P-wave window 342, Block 400, as described above, and determines whether a maximum amplitude of the P-wave located within the window 342, Block 402, is greater than an amplitude threshold, Block 404. If the maximum amplitude is not greater than the maximum amplitude threshold, No in Block 404, the waveform is determined not to be a P-wave, Block 406, the current four P-waves are therefore discarded, and the process is repeated with the next four determined P-waves.

If the maximum amplitude is greater than the maximum amplitude threshold, Yes in Block 404, the device determines the adjusted P-wave, Block 408, and the normalized P-wave parameters, Block 410, resulting from the normalized P-wave window 386, such as the width 382 and amplitude 388 of the normalized P-wave center window 386, described above. When the determination of Blocks 400-410 has been made for each of the four P-waves 328, No in Block 412, the device utilizes the determined parameters to determine an average P-wave width 382, Block 414, and an average P-wave normalized amplitude 388, Block 416, for the four P-waves 328. A determination is then made for each of the P-waves 328, as to whether each of the P-waves 328 match each other within a predetermined P-wave match threshold, Block 418, indicative of the likelihood that the waveform is a P-wave.

Figure 10:
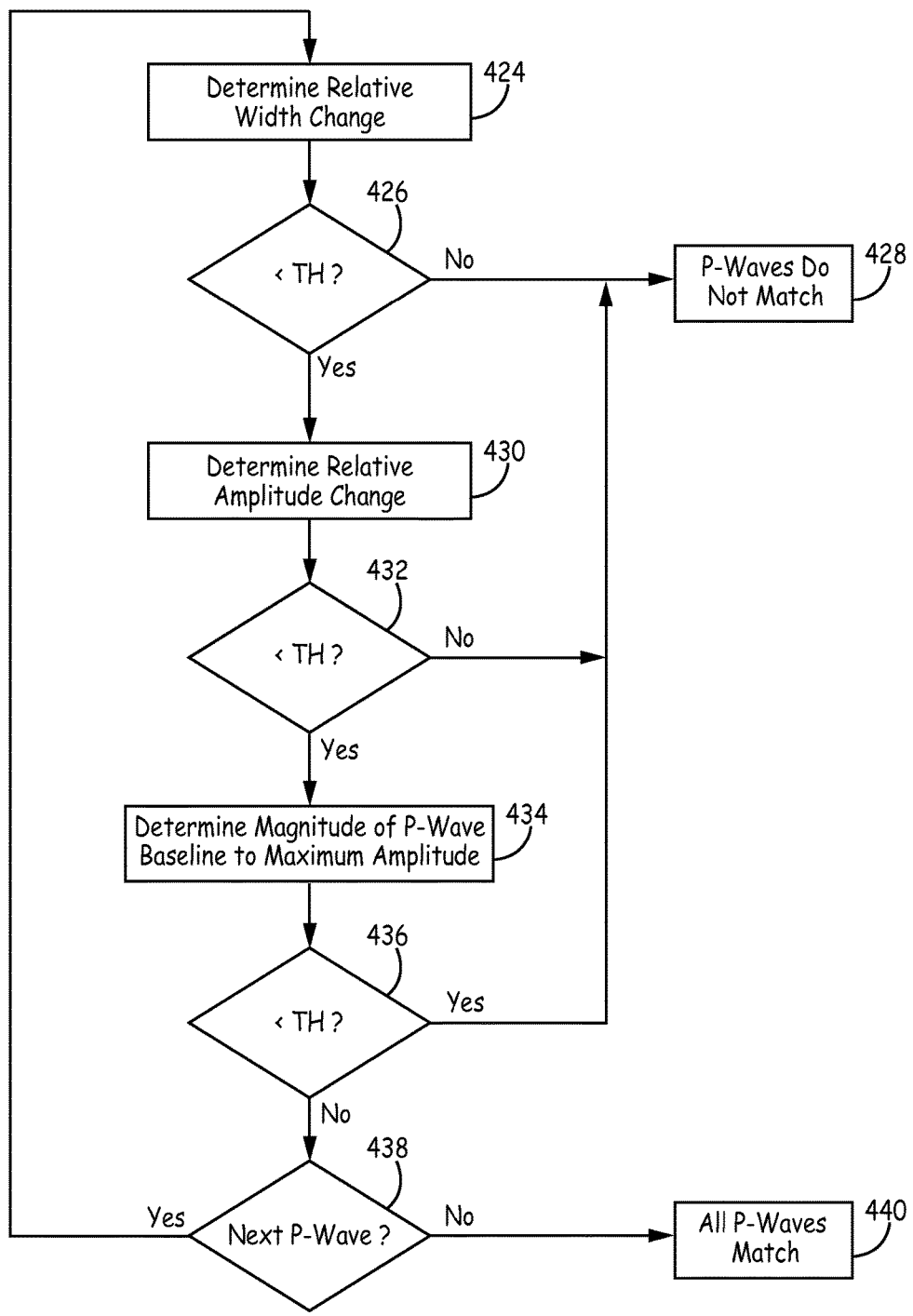
FIG. 10 is a flowchart of determining P-wave matching in a medical device according to an embodiment of the present disclosure.

FIG. 10 is a flowchart of determining P-wave matching in a medical device according to an embodiment of the present disclosure. According to one embodiment, in order to make the determination as to whether a P-wave 328 matches the P-wave threshold in Block 418, the device determines, for each one of the four P-waves, a corresponding relative width change, Block 424, by determining the absolute value of the difference between the width associated with baseline 382 extending between points 376 and 378 of the adjusted P-wave 372 for each P-wave 328, and the average width determined for the four P-waves (Block 414 of FIG. 9). The width change is compared to a width change threshold, Block 426, and if the width change is not less than the width change threshold, No in Block 426, the waveform is determined not to be a P-wave, Block 428, and the next four R-waves and corresponding P-waves are determined, as described above, and the process is repeated using the next four P-waves.

If the width change is less than the width change threshold, Yes in Block 426, the device determines a relative normalized amplitude change for the P-wave, Block 430, by determining the absolute value of the difference between the maximum normalized amplitude 388 of the P-wave 372 and the average amplitude determined for the current four P-waves (Block 416 of FIG. 9). The amplitude change is compared to an amplitude change threshold, Block 432, and if the amplitude change is not less than the amplitude change threshold, No in Block 432, the waveform is determined not to be a P-wave, Block 428, and the next four R-waves and corresponding P-waves are determined, as described above, and the process is repeated using the next four P-waves. If the amplitude change is determined to be less than the amplitude change threshold, Yes in Block 432, the device determines the magnitude of the P-wave by determining the distance between the baseline 382 and the maximum amplitude 374, Block 434, and compares the determined P-wave magnitude to a magnitude threshold, Block 436. If the P-wave magnitude is less than the magnitude threshold, Yes in Block 436, the waveform is determined not to be a P-wave, Block 428, and the next four R-waves and corresponding P-waves are determined, as described above, and the process is repeated using the next four P-waves. If the P-wave magnitude is not less than the magnitude threshold, No in Block 436, the P-wave is determined to match the P-wave threshold, and the process is repeated with the next P-wave 328 until all four P-waves 323 have been determined to match the P-wave threshold, Block 440.

According to one embodiment, the width change threshold and the amplitude change threshold are set equal to 62.5 percent, and the magnitude threshold is set as 50 percent, for example.

Returning to FIG. 9, if all four of the P-waves 328 are determined to match the P-wave threshold using the process described in FIG. 10, Yes in block 418, the device aligns the peaks of three of the P-waves to the peak of the remaining P-wave using the determined center of areas 382. For example, according to one embodiment, the last three P-waves are aligned to the first P-wave. The device determines an average P-wave resulting from the aligned P-waves, which is then set as the P-wave template, Block 422, for subsequent use in identifying P-waves.

Figure 11A:
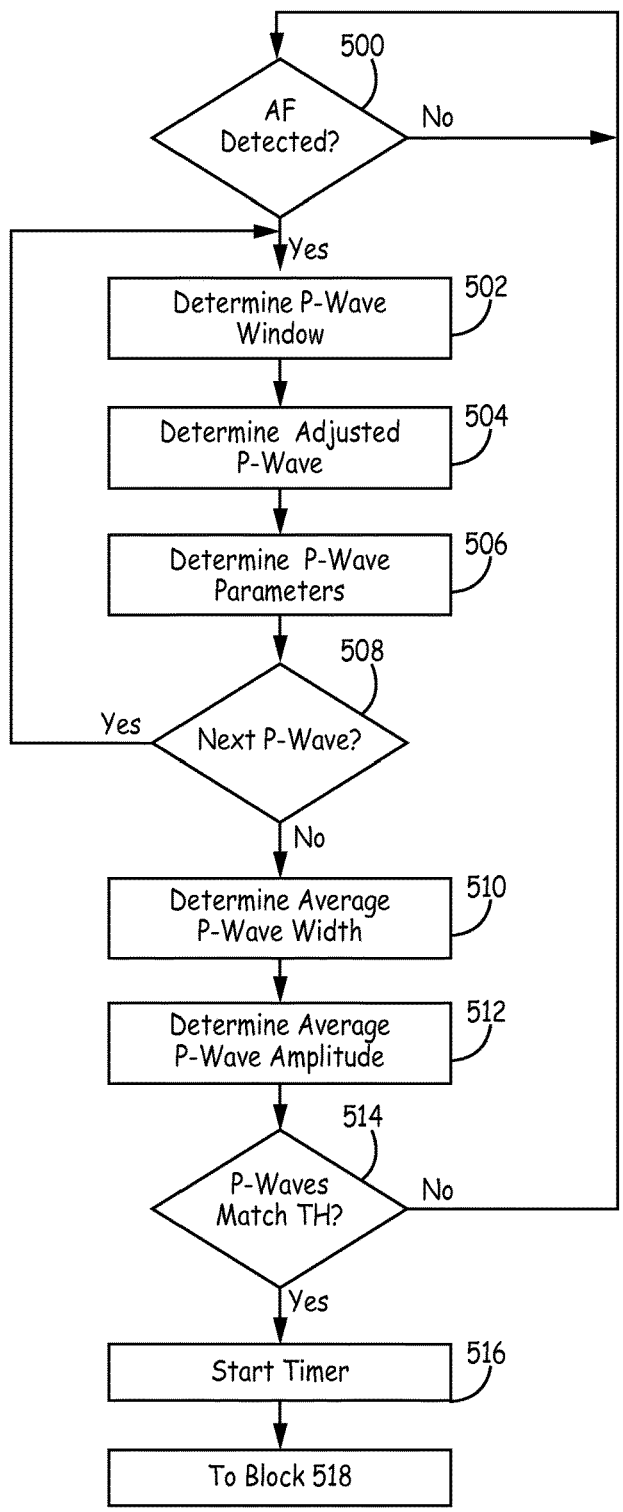
FIGS. 11A and 11B are flowcharts of detecting an atrial arrhythmia in a cardiac medical device according to an embodiment of the present disclosure.
Figure 11B:
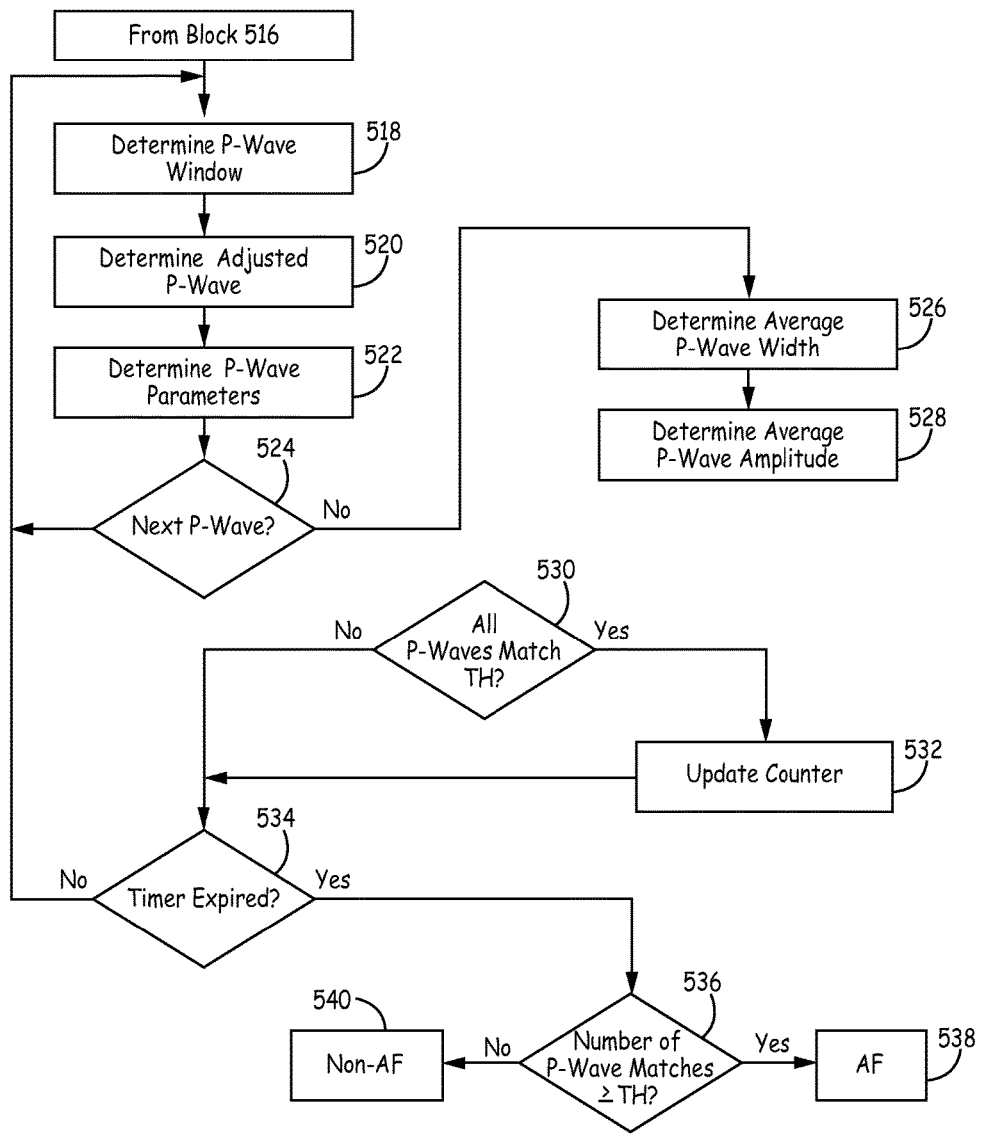

FIGS. 11A and 11B are flowcharts of detecting an atrial arrhythmia in a cardiac medical device according to an embodiment of the present disclosure. As illustrated in FIGS. 11A and 11B, according to one embodiment, the device identifies an AF arrhythmia event using any known AF detection scheme, such as the AF detection scheme described above, for example. As illustrated in FIG. 11A, upon detection of an AF event, Block 500, the device identifies four slow, non-paced beats, resulting in four R-waves, and using the process described above, determines a P-wave window, Block 502, and an adjusted P-wave, Block 504, for each R-wave, along with P-wave parameters, Block 506, such as the width 382 and the normalized amplitude 388 associated with the adjusted P-wave 372. When the parameters 506 have been determined for all four P-waves, Yes in Block 508, the device utilizes the determined parameters to determine an average P-wave width, Block 510, based on an average of the four P-wave widths, and an average P-wave amplitude, Block 512, based on the average of the four P-wave amplitudes. A determination is then made for each of the P-waves as to whether each of the P-waves match each other within a predetermined P-wave match threshold, Block 514, indicative of the likelihood that the waveform is a P-wave.

According to one embodiment, in order to make the determination as to whether a P-wave matches the P-wave threshold in Block 514, the device determines, in a manner similar to the scheme for generating a P-wave template described above, a corresponding relative width change, a relative amplitude change, and a P-wave magnitude for each one of the four P-waves. In particular, order to determine the width change, the device determines the absolute value of the difference between the width associated with baseline 382 of the adjusted P-wave 372 for each P-wave and the average width determined for the four P-waves. The width change is then compared to a width change threshold. To determine the amplitude change, the device determines the absolute value of the difference between the maximum normalized amplitude 388 of the P-wave 328 and the average normalized amplitude determined for the current four P-waves 328, and compares the normalized amplitude change to an amplitude change threshold. Finally, in order to determine the magnitude of the P-wave the device determines the distance between the baseline 382 and the maximum amplitude 374 for each of the P-waves, and compares the determined P-wave magnitude to a magnitude threshold.

If, for any one of the P-waves, either the width change is not less than the width change threshold, the amplitude change is not less than the amplitude change threshold, or the P-wave magnitude is less than the magnitude threshold, the waveform is determined not to be a P-wave, and therefore all of P-waves do not match the P-wave threshold, No in Block 514. As a result, if the AF event continues to be detected, Yes in Block 500, the device determines the next four R-waves and corresponding P-waves are determined, as described above, and the process 502-512 is repeated using the next four P-waves. On the other hand if the width change is less than the width change threshold, the amplitude change is less than the amplitude change threshold, and the P-wave magnitude is not less than the magnitude threshold for each of the P-waves, the P-waves are determined to match the P-wave threshold, Yes in Block 514, and a timer is initiated, Block 516.

According to one embodiment, during AF detection the width change threshold and the amplitude change threshold are set equal to 50 percent, the magnitude threshold is set as 50 percent, and the timer Block 516 is set as two minutes, for example.

As Illustrated in FIG. 11B, when the timer is initiated, Block 516, the device identifies the next four slow, non-paced beats, resulting in four R-waves, and using the process described above, determines a P-wave window, Block 518 and an adjusted P-wave, Block 520, for each R-wave, along with P-wave parameters, Block 522, such as the width 382 and the normalized amplitude 388 of the adjusted P-wave 372. When the P-wave parameters have been determined, Block 522, for all four P-waves, Yes in Block 524, the device utilizes the determined parameters to determine an average P-wave width, Block 526, based on an average of the four P-wave widths, and an average P-wave normalized amplitude, Block 528, based on the average of the four P-wave normalized amplitudes. A determination is then made for each of the P-waves as to whether each of the P-waves match each other within a predetermined P-wave match threshold, Block 530, indicative of the likelihood that the waveform is a P-wave.

According to one embodiment, in order to make the determination as to whether a P-wave matches the P-wave threshold in Block 530, the device determines, in a manner similar to described above, a corresponding relative width change, and a relative normalized amplitude change for each one of the four P-waves, along with a P-wave magnitude. In particular, order to determine the width change, the device determines the absolute value of the difference between the width associated with baseline 382 of the adjusted P-wave 372 for each P-wave, and the average width determined for the four P-waves, and compares the width change to a width change threshold. To determine the normalized amplitude change, the device determines the absolute value of the difference between the maximum normalized amplitude 388 of the adjusted P-wave 372 and the average normalized amplitude determined for the current four P-waves 328, and compares the amplitude change to an amplitude change threshold. Finally, in order to determine the magnitude of the P-wave the device determines the distance between the baseline 382 and the maximum amplitude 374 for each of the P-waves, and compares the determined P-wave magnitude to a magnitude threshold.

If, for any one of the P-waves, either the width change is not less than the width change threshold, the amplitude change is not less than the amplitude change threshold, or the P-wave magnitude is less than the magnitude threshold, the waveform is determined not to be a P-wave, and therefore all of P-waves do not match the P-wave threshold, No in Block 530. On the other hand if the width change is less than the width change threshold, the amplitude change is less than the amplitude change threshold, and the P-wave magnitude is not less than the magnitude threshold for each of the four P-waves, all of P-waves are determined to match the P-wave threshold, Yes in Block 514, and a counter, counter the number of times four P-waves are determined to match the P-wave threshold, Yes in Block 530, is increased by one, is increased, Block 532.

When either the four P-waves match the P-wave threshold, Yes in Block 530, and the counter has been update, or the four P-waves do not match the P-wave threshold, No in Block 530, the device determine whether the timer has expired, Bock 534. If the timer has not expired, No in Block 534, and if the AF event continues to be detected, Yes in Block 500, the device determines the next four R-waves and corresponding P-waves are determined, as described above, and the process 502-512 is repeated using the next four P-waves. If the timer has expire, Yes in Block 534, the device determines whether the number of times, i.e, the value of the counter, Block 532, that the four P-waves were determined to match the P-wave threshold, Yes in Block 530, during the given time period is greater than or equal to a match threshold, Block 536. If the number of times that the four P-waves match the P-wave threshold during the given time period is greater than or equal to a match threshold, Yes in Block 536, the event is determined to be an AF event, and the device may perform any function or combination of functions, such as delivering a therapy, sounding an alarm, storing the determination of an AF event within the device, or transmitting the determination, etc. If the number of times that the four P-waves match the P-wave threshold during the given time period is not greater than or equal to a match threshold, No in Block 536, the event is determined to be a non-AF event, Bock 540.

According to one embodiment, during AF detection the width change threshold and the amplitude change threshold are set equal to 62.5 percent, the magnitude threshold is set as 50 percent, the timer Block 516 is set as two minutes, and the match threshold is set as two, for example.

Figure 12:
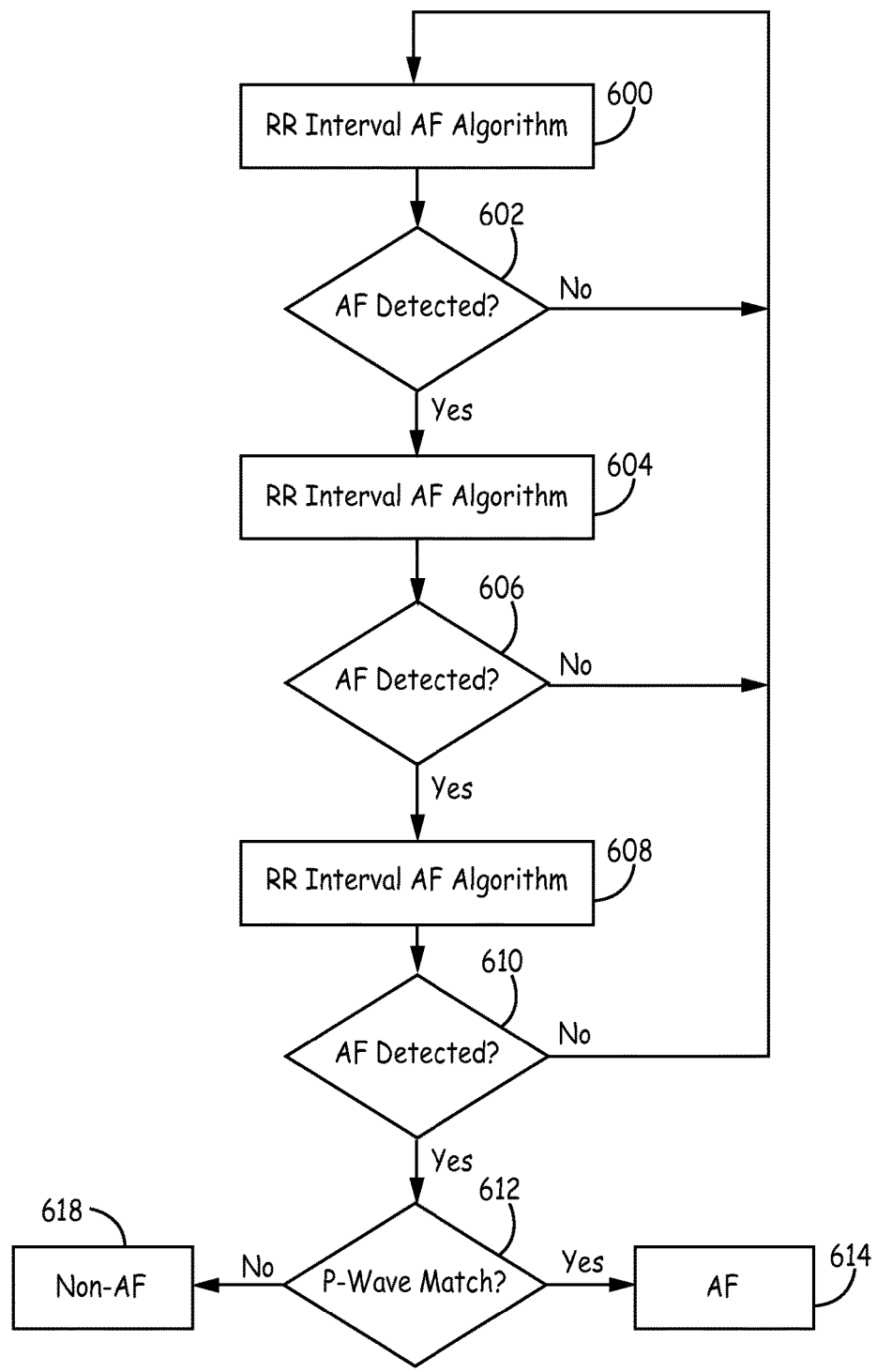
FIG. 12 is a flowchart of a method of detecting an atrial arrhythmia in a medical device according to an embodiment of the present disclosure.

FIG. 12 is a flowchart of a method of detecting an atrial arrhythmia in a medical device according to an embodiment of the present disclosure. As illustrated in FIG. 12, according to one embodiment, in order to identify an AF arrhythmia event, the device determines an AF score over a predetermined time period, Block 600, using the RR-interval AF algorithm described above, for example, and determines, based on the AF score once the time period has expired, whether an AF event is detected, Block 602. According to one embodiment, in order to enhance RR-interval based AF detection specificity, if an AF event is detected, Yes in Block 602, the device determines an AF score over the time period again, Block 604. If an AF event has been detected based on AF scores determined over two of the time periods, Blocks 600 and 604, Yes in Block 606, the device determines an AF score a third time over the time period, Block 608, and if the AF event is determined as occurring the third time, Yes in Block 610, the device performs the confirmation of the AF detection using the P-wave analysis, Block 612, over the time period or subsequent to the time period, using the P-wave detection scheme described above. According to one embodiment, the time period may be set as two minutes, for example.

If the P-wave analysis determines the event as being an AF event, Yes in Block 612, a response to the AF detection may include withholding or altering therapy, such as a ventricular therapy, for example, storing data that can be later retrieved by a clinician, triggering an alarm to the patient or that may be sent remotely to alert the clinician, delivering or adjusting a therapy, and triggering other signal acquisition or analysis.

It is understood that while the embodiment illustrated in FIG. 12 indicates detection of an AF event taking place over three separate two minute time periods, with the P-wave analysis being include with the third time period, Block 608, other embodiments could include one, two or more than two repeated AF detection analyses, and that the P-wave analysis could be included with any one or combinations of the AF determinations. It is also understood that the P-wave template may be generated either manually during device implant or during an office visit by the patient, and that the template may be automatically updated (e.g., daily or weekly) by the device. Furthermore, the method may be applied in any device utilizing an intracardiac EGM, Sub-cutaneous ECG or surface ECG vectors, and other implanted or external cardiac rhythm devices Thus, an apparatus and method have been presented in the foregoing description with reference to specific embodiments. It is appreciated that various modifications to the referenced embodiments may be made without departing from the scope of the invention as set forth in the following claims.

We claim:

1. A method of identifying a cardiac waveform in a medical device, comprising:
   sensing cardiac signals;
   identifying R-waves in the cardiac signal;
   determining P-waves associated with each of the identified R-waves;
   determining one or more parameters associated with each of the determined P-waves;
   determining relative changes of the determined P-waves based on the one or more determined parameters;
   determining whether each of the determined P-waves match within a match threshold based on the determined relative changes; and
   generating a P-wave template based on the determined P-waves in response to determining that each of the determined P-waves match within the match threshold.

2. The method of claim 1, further comprising:
   determining a P-wave window associated with each of the identified R-waves;
   adjusting the determined P-waves within each of the P-wave windows; and
   wherein determining the one or more P-wave parameters comprises determining the one or more parameters associated with each of the adjusted P-waves.

3. The method of claim 2, further comprising:
   determining, for each of the P-wave windows, a start point and an end point extending a predetermined distance from the start point based on the associated R-wave;
   determining a first baseline window based on the start point and a second baseline window based on the end point; and
   determining a first baseline end point within the first baseline window and a second baseline endpoint within the second baseline window, wherein adjusting the determined P-waves comprises adjusting a slope of a baseline extending between the first baseline end point and the second baseline end point.

4. The method of claim 1, further comprising:
   determining, for each of the P-wave windows, a maximum amplitude;
   determining, for each of the determined P-waves, a first minimum baseline point and a second minimum baseline point as a portion of the maximum amplitude;
   determining, for each of the P-wave windows, an area based on a baseline extending between the first minimum baseline point and the second minimum baseline point;
   normalizing each of the determined P-waves based on the area and the baseline; and
   generating the template using the normalized P-waves.

5. The method of claim 4, wherein normalizing the determined P-waves comprises:
   determining a normalized amplitude of each of the normalized P-waves;
   determining a center of the area of each of the normalized P-waves based on a width of the baseline and the normalized amplitude; and
   generating the template based on the center of area of each of the normalized P-waves.

6. The method of claim 1, wherein determining relative changes of the P-waves comprises:
   determining a width change for each of the determined P-waves;
   determining an amplitude change for each of the determined P-waves;
   determining a magnitude change for each of the determined P-waves; and
   wherein determining whether each of the determined P-waves match comprises determining that the determined P-waves match when each of the determined width changes, the determined amplitude changes and the determined magnitude changes are within the match threshold.

7. The method of claim 6, further comprising:
   determining a P-wave window associated with each of the identified R-waves;
   adjusting the determined P-waves within each of the P-wave windows; and
   wherein determining the one or more P-wave parameters comprises determining the one or more parameters associated with each of the adjusted P-waves.

8. The method of claim 7, further comprising:
   determining, for each of the determined P-waves, a start point and an end point extending a predetermined distance from the start point based on the associated R-wave;

determining a first baseline window based on the start point and a second baseline window based on the end point; and determining a first baseline end point within the first baseline window and a second baseline endpoint within the second baseline window, wherein adjusting the determined P-waves comprises adjusting a slope of a baseline extending between the first baseline end point and the second baseline end point.

9. The method of claim 1, wherein determining relative changes of the determined P-waves comprises:

determining a width of the baseline for each determined P-wave;

determining an average width based on the width determined for each determined P-wave;

comparing the width of each determined P-wave to the average width to determine a width change for each of the determined P-waves;

determining a normalized amplitude of each of the determined P-waves;

determining an average normalized amplitude based on the normalized amplitude determined for each of the determined P-waves;

comparing the normalized amplitude of each determined P-wave to the average normalized amplitude to determine an amplitude change for each of the determined P-waves;

determining a distance between the maximum amplitude and the baseline for each of the determined P-waves;

comparing the distance between the maximum amplitude and the baseline to a magnitude threshold to determine a magnitude change for each of the determined P-waves; and determining whether to generate the template with the determined P-waves based on the determined width changes, the determined amplitude changes and the determined magnitude changes.

10. The method of claim 9, further comprising:

determining a P-wave window associated with each of the identified R-waves;

adjusting the determined P-waves within each of the P-wave windows; and wherein determining the one or more P-wave parameters comprises determining the one or more parameters associated with each of the adjusted P-waves.

11. The method of claim 10, further comprising:

determining, for each of the P-wave windows, a start point and an end point extending a predetermined distance from the start point based on the associated R-wave;

determining a first baseline window based on the start point and a second baseline window based on the end point; and determining a first baseline end point within the first baseline window and a second baseline endpoint within the second baseline window, wherein adjusting the determined P-waves comprises adjusting a slope of a baseline extending between the first baseline end point and the second baseline end point.

12. The method of claim 1, further comprising excluding the determined P-waves from the generation of the P-wave template in response to determining that any of the determined P-waves do not match within the match threshold.

13. The method of claim 1, further comprising delivering or adjusting, via the medical device, a therapy to a heart based on comparing a cardiac signal of a ventricle of the heart to the P-wave template.

14. The method of claim 1, further comprising:

detecting or confirming atrial fibrillation based on comparing the cardiac signal to the P-wave template; and withholding or altering a ventricular therapy based on detecting or confirming the atrial fibrillation.

15. A medical device for detecting a cardiac event, comprising:

a sense amplifier configured to obtain a cardiac signal via at least one sensing electrode; and a processor configured to identify R-waves in the sense cardiac signal, determine P-waves associated with each of the identified R-waves, determine one or more parameters associated with each of the determined P-waves, determine relative changes of the determined P-waves based on the one or more determined parameters, determine whether each of the determined P-waves match within a match threshold in response to the determined relative changes, and generate a P-wave template based on the determined P-waves in response to determining that each of the determined P-waves match within the match threshold.

16. The device of claim 15, wherein the processor is further configured to determine a P-wave window associated with each of the identified R-waves, adjust the determined P-waves within each of the P-wave windows, and determine the one or more P-wave parameters of the adjusted P-waves.

17. The device of claim 16, wherein the processor is further configured to determine, for each of the P-wave windows, a start point and an end point extending a predetermined distance from the start point based on the associated R-wave, determine a first baseline window based on the start point and a second baseline window based on the end point, and determine a first baseline end point within the first baseline window and a second baseline endpoint within the second baseline window, wherein adjusting the determined P-waves comprises adjusting a slope of a baseline extending between the first baseline end point and the second baseline end point.

18. The device of claim 15, wherein the processor is further configured to determine, for each of the determined P-waves, a maximum amplitude, determine, for each of the determined P-waves, a first minimum baseline point and a second minimum baseline point as a portion of the maximum amplitude, determine, for each of the determined P-waves, an area based on a baseline extending between the first minimum baseline point and the second minimum baseline point, normalize each of the determined P-waves based on the area and the baseline, and generate the template using the normalized P-waves.

19. The device of claim 18, wherein normalizing the determined P-waves comprises:

determining a normalized amplitude of each of the normalized P-waves;

determining a center of the area of each of the normalized P-waves based on a width of the baseline and the normalized amplitude; and generating the template based on the center of area of each of the normalized P-waves.

20. The device of claim 15, wherein the processor determines the relative changes of the determined P-waves by:

determining a width change for each of the determined P-waves;

determining an amplitude change for each of the determined P-waves;

determining a magnitude change for each of the determined P-waves; and wherein determining whether each of the determined P-waves match comprises determining that the P-waves match when each of the determined width changes, the determined amplitude changes and the determined magnitude changes are within the match threshold.

21. The device of claim 20, wherein the processor is further configured to determine a P-wave window associated with each of the identified R-waves, adjust the determined P-waves within each of the P-wave windows, and determine the one or more P-wave parameters of the adjusted P-waves.

22. The device of claim 21, wherein the processor is further configured to determine, for each of the P-wave windows, a start point and an end point extending a predetermined distance from the start point based on the associated R-wave, determine a first baseline window based on the start point and a second baseline window based on the end point and determine a first baseline end point within the first baseline window and a second baseline endpoint within the second baseline window, wherein adjusting the determined P-waves comprises adjusting a slope of a baseline extending between the first baseline end point and the second baseline end point.

23. The device of claim 15, wherein the processor determines the relative changes of the determined P-waves by:
  determining a width of the baseline for each determined P-wave;
  determining an average width based on the width determined for each determined P-wave;
  comparing the width of each determined P-wave to the average width to determine a width change for each of the determined P-waves;
  determining a normalized amplitude of each of the determined P-waves;
  determining an average normalized amplitude based on the normalized amplitude determined for each of the determined P-waves;
  comparing the normalized amplitude of each determined P-wave to the average normalized amplitude to determine an amplitude change for each of the determined P-waves;
  determining a distance between the maximum amplitude and the baseline for each of the determined P-waves;
  comparing the distance between the maximum amplitude and the baseline to a magnitude threshold to determine a magnitude change for each of the determined P-waves; and
  determining whether to generate the template with the determined P-waves based on the determined width changes, the determined amplitude changes and the determined magnitude changes.

24. The device of claim 23, wherein the processor is further configure to determine a P-wave window associated with each of the identified R-waves, adjust the determined P-waves within each of the P-wave windows, and determine the one or more P-wave parameters of the adjusted P-waves.

25. The device of claim 24, wherein the processor is further configured to determine, for each of the P-wave windows, a start point and an end point extending a predetermined distance from the start point based on the associated R-wave, determine a first baseline window based on the start point and a second baseline window based on the end point, and determine a first baseline end point within the first baseline window and a second baseline endpoint within the second baseline window, wherein adjusting the determined P-waves comprises adjusting a slope of a baseline extending between the first baseline end point and the second baseline end point.

26. The device of claim 15, further comprising an output circuit to deliver therapy to a heart via an electrode based at least in part to comparing the cardiac signal to the generated template.

27. A non-transitory, computer-readable storage medium storing instructions for causing a processor included in a medical device to perform a method for identifying a cardiac waveform, the method comprising:
  sensing cardiac signals;
  identifying R-waves in the cardiac signal;
  determining P-waves associated with each of the identified R-waves;
  determining one or more parameters associated with each of the determined P-wave;
  determining relative changes of the determined P-waves based on the one or more determined parameters;
  determining whether each of the determined P-waves match within a match threshold based on the determined relative changes; and
  generating a P-wave template in response to determining that each of the determined P-waves matching within the match threshold.

28. A cardiac medical device for detecting a cardiac event and delivering a therapy for treating atrial fibrillation, comprising:
  a sense amplifier configured to obtain a cardiac signal associated only with a ventricle of a heart;
  a processor configured to identify R-waves in the sensed cardiac signals, determine P-waves associated with each of the identified R-waves, determine one or more parameters associated with each of the determined P-waves, determine relative changes of the determined P-waves based on the one or more determined parameters, determine whether each of the determined P-waves match within a match threshold in response to the determined relative changes, and generate a P-wave template based on the determined P-waves in response to determining that each of the determined P-waves match within the match threshold; and
  an output circuit to deliver therapy to the heart via an electrode based at least in part to comparing the cardiac signal to the generated template.

29. The device of claim 28, wherein the processor is further configured to determine whether atrial fibrillation is occurring in response to the sensed cardiac signal, and deliver ventricular pacing therapy via the output circuit during the detecting a cardiac event.

30. The device of claim 28, wherein the processor is further configured to determine, for each of the determined P-waves, a maximum amplitude, determine, for each of the determined P-waves, a first minimum baseline point and a second minimum baseline point as a portion of the maximum amplitude, determine, for each of the determined P-waves, an area based on a baseline extending between the first minimum baseline point and the second minimum baseline point, normalize each of the determined P-waves based on the area and the baseline, and generate the template using the normalized P-waves.

31. The device of claim 28, wherein the processor determines the relative changes of the determined P-waves by:
  determining a width of the baseline for each determined P-wave;
  determining an average width based on the width determined for each determined P-wave;

comparing the width of each determined P-wave to the average width to determine a width change for each of the determined P-waves;

determining a normalized amplitude of each of the determined P-waves;

determining an average normalized amplitude based on the normalized amplitude determined for each of the determined P-waves;

comparing the normalized amplitude of each determined P-wave to the average normalized amplitude to determine an amplitude change for each of the determined P-waves;

determining a distance between the maximum amplitude and the baseline for each of the determined P-waves;

comparing the distance between the maximum amplitude and the baseline to a magnitude threshold to determine a magnitude change for each of the determined P-waves; and determining whether to generate the template with the determined P-waves based on the determined width changes, the determined amplitude changes and the determined magnitude changes.

32. The device of claim 31, wherein the processor is further configure to determine a P-wave window associated with each of the identified R-waves, adjusting the determined P-waves within each of the P-wave windows, and determine the one or more P-wave parameters of the adjusted P-waves.

33. The device of claim 32, wherein the processor is further configured to determine, for each of the P-wave windows, a start point and an end point extending a predetermined distance from the start point based on the associated R-wave, determine a first baseline window based on the start point and a second baseline window based on the end point, and determine a first baseline end point within the first baseline window and a second baseline endpoint within the second baseline window, wherein adjusting the determined P-waves comprises adjusting a slope of a baseline extending between the first baseline end point and the second baseline end point.

* * * * *